US006576133B2

(12) United States Patent
Gjerde et al.

(10) Patent No.: US 6,576,133 B2
(45) Date of Patent: *Jun. 10, 2003

(54) METHOD AND SYSTEM FOR RNA ANALYSIS BY MATCHED ION POLYNUCLEOTIDE CHROMATOGRAPHY

(75) Inventors: Douglas T. Gjerde, Saratoga, CA (US); David P. Hornby, Widnes (GB); Christopher P. Hanna, Greenfield, MA (US); Alexander I. Kuklin, Blue Bell, PA (US); Robert M. Haefele, Campbell, CA (US); Paul D. Taylor, Gilroy, CA (US)

(73) Assignee: Transgenomic, INC, Omaha, NE (US)

( * ) Notice: Subject to any disclaimer, the term of this patent is extended or adjusted under 35 U.S.C. 154(b) by 89 days.

This patent is subject to a terminal disclaimer.

(21) Appl. No.: 09/753,856

(22) Filed: Jan. 2, 2001

(65) Prior Publication Data

US 2001/0042714 A1 Nov. 22, 2001

Related U.S. Application Data

(63) Continuation-in-part of application No. 09/557,424, filed on Apr. 21, 2000, now Pat. No. 6,475,388, which is a continuation-in-part of application No. 09/183,123, filed on Oct. 30, 1998, now Pat. No. 6,066,258, which is a continuation-in-part of application No. 09/058,580, filed on Apr. 10, 1998, now abandoned, which is a continuation-in-part of application No. 08/748,376, filed on Nov. 13, 1996, now Pat. No. 5,772,889.
(60) Provisional application No. 60/187,979, filed on Mar. 9, 2000, provisional application No. 60/224,918, filed on Aug. 11, 2000, provisional application No. 60/215,208, filed on Jun. 29, 2000, and provisional application No. 60/220,119, filed on Jul. 21, 2000.

(51) Int. Cl.[7] .............................................. B01D 15/08
(52) U.S. Cl. .................... 210/635; 210/656; 210/198.2; 435/6; 536/25.4
(58) Field of Search ............................ 210/635, 656, 210/659, 198.2; 435/6; 536/23.1, 25.4

(56) References Cited

U.S. PATENT DOCUMENTS 4,563,510 A    1/1986  Ugelstad ..................... 526/66

(List continued on next page.)

FOREIGN PATENT DOCUMENTS

EP    0 507 591 A2    10/1992    .................. 210/656

(List continued on next page.)

OTHER PUBLICATIONS

AbouHaidar et al. Non–Enzymatic RNA Hydrolysis Promoted by the Combined Catalytic Activity of Buffers and Magnesium Ions, Z. Naturforsch 54c, 542–548 (1999).

(List continued on next page.)

*Primary Examiner*—Ernest G. Therkorn
(74) *Attorney, Agent, or Firm*—Keith A. Johnson

(57) ABSTRACT

A Matched Ion Polynucleotide Chromatography method and system for size-based segregation of a mixture of RNA molecules. The method includes applying the mixture to a polymeric separation medium having non-polar surfaces and eluting the RNA molecules with a mobile phase which includes counterion reagent and an organic component. The preferred surfaces are characterized by being substantially free from multivalent cations which are free to interfere with RNA segregation. The elution is preferably performed at a temperature sufficient to denature the RNA. The method can be used in segregating RNA molecules having lengths in the range of about 100 to 20,000 nucleotides. Improved segregation is obtained using a chromatography column having an ID greater than about 5 mm. Examples of separation media include beads and monolithic columns.

48 Claims, 17 Drawing Sheets

U.S. PATENT DOCUMENTS

| | | | |
|---|---|---|---|
| 4,906,378 A | 3/1990 | Hagan et al. | 210/635 |
| 5,334,310 A | 8/1994 | Frechet et al. | 210/198.2 |
| 5,336,412 A | 8/1994 | Huse et al. | 210/635 |
| 5,338,448 A | 8/1994 | Gjerde | 210/198.2 |
| 5,378,359 A | 1/1995 | Huse et al. | 210/198.2 |
| 5,378,360 A | 1/1995 | Huse et al. | 210/198.2 |
| 5,413,708 A | 5/1995 | Huse et al. | 210/198.2 |
| 5,438,128 A | 8/1995 | Nieuwkerk et al. | 536/25.4 |
| 5,453,185 A | 9/1995 | Frechet et al. | 210/198.2 |
| 5,522,994 A | 6/1996 | Frechet et al. | 210/635 |
| 5,559,001 A | 9/1996 | Utermohlen | 435/6 |
| 5,585,236 A | 12/1996 | Bonn et al. | 435/5 |
| 5,677,124 A | 10/1997 | DuBois et al. | 435/5 |
| 5,772,889 A | 6/1998 | Gjerde et al. | 210/198.2 |
| 5,795,752 A | 8/1998 | Smith | 435/172.3 |
| 5,795,976 A | 8/1998 | Oefner | 536/25.4 |
| 5,837,520 A | 11/1998 | Shabram et al. | 435/239 |
| 5,945,515 A | 8/1999 | Chomczynski | 530/412 |
| 5,972,222 A | 10/1999 | Gjerde et al. | 210/198.2 |
| 5,973,137 A | 10/1999 | Heath | 536/25.4 |
| 5,986,085 A | 11/1999 | Gjerde et al. | 536/25.4 |
| 5,997,742 A | 12/1999 | Gjerde et al. | 210/635 |
| 5,998,604 A | 12/1999 | Fearon et al. | 536/25.4 |
| 5,998,605 A | 12/1999 | Chamberlain et al. | 536/27.11 |
| 6,017,457 A | 1/2000 | Gjerde et al. | 210/635 |
| 6,024,878 A | 2/2000 | Gjerde et al. | 210/635 |
| 6,030,527 A | 2/2000 | Gjerde et al. | 210/198.2 |
| 6,056,877 A | 5/2000 | Gjerde et al. | 210/635 |
| 6,066,258 A | 5/2000 | Gjerde et al. | 210/635 |
| 6,177,559 B1 | 1/2001 | Gjerde et al. | 536/25.4 |
| 6,265,168 B1 | 1/2001 | Gjerde et al. | 436/6 |
| 6,238,565 B1 | 5/2001 | Hatch | 210/635 |
| 6,372,142 B1 | 4/2002 | Gjerde et al. | 210/635 |
| 6,419,824 B1 | 7/2002 | Gjerde | 210/198.2 |

FOREIGN PATENT DOCUMENTS

| | | | | |
|---|---|---|---|---|
| WO | WO 98/40395 | 9/1998 | | 210/656 |
| WO | WO 98/48913 | 11/1998 | | 210/656 |
| WO | WO 98/48914 | 11/1998 | | 210/656 |
| WO | WO 98/56797 | 12/1998 | | 210/656 |
| WO | WO 98/56798 | 12/1998 | | 210/656 |
| WO | WO 00/15778 | 3/2000 | | 210/656 |
| WO | WO 01/02418 A1 | 1/2001 | | 210/656 |
| WO | WO 01/66216 | 9/2001 | | 216/635 |

OTHER PUBLICATIONS

All–Chrom Newsletter, Metal Components, A Potential Source of Interference in HPLC Analysis, Alltech–Applied Science, 25: 1–6 (1986).

Ambion Technical Bulletin 159, Working With RNA, downloaded from www.ambion.com on Jun. 4, 2001.

Ambion Technical Bulletin 166, Nuclease and Protease Testing: Laboratory and Commercial Considerations, downloaded from www.ambion.com on Jun. 4, 2001.

Ambion Technical Bulletin 178, RNASE and DEPC Treatment: Fact or Laboratory Myth, downloaded from www.ambion.com on Jun. 4, 2001.

Ambion Technical Bulletin 180, How to Maintain an RNASE–Free Lab, downloaded from www.ambion.com on Jun. 4, 2001.

Arends et al. Partial Purification and Characterization of Nuclear Ribonuclease P From Wheat, Eur J. Biochem. 244:635–645 (1997).

Ausubel, F.M. et al. Current Protocols in Molecular Biology, John Wiley & Sons, pp. 4.0.1—4.10.11 (1995) Eds.

Azarani A. et al., RNA Analysis by Ion–Pair Reversed–Phase HPLC, Proceedings of the 2000 Miami Nature Biotechnology Winter Symposium, Miami Nature Biotechnology Short Reports, Oxford University Press, 11:29(2000).

Baba, Yoshinobu et al. Journal of Chromatography 618:41–55(1993).

Bischoff et al. Isolation of Specific tRNAs Using an Ionic–Hydrophobic Mixed–Mode Chromatographic Matrix, Analytical Biochemistry, 151:526–533 (1985).

Bishop et al. Conformational Effects of Reversed–Phase HPLC on Ribonuclease a and x–Chymotryspin by Prarticle Beam LC/FT–IR Spectrometry, Mikrochim. Actu [Suppl.] 14:721–724 (1997).

Bulychev NV, et al., Bioorg Khim, 14:27–30 (1988).

Cotton et al. Reactivity of Cytosine ANS Thymine in Single–Base–Pair Mismatches with Hydrozylamine an Osmium Tetroxide and its Application to the Stury of Mutations, Proc. Natl. Acad. Sci. USA, 85: 4397–4401 (1988).

Dell'Anno et al. Nucleic Acid (DNA, RNA) Quantification and RNA/DNA Ratio Determination in Marine Sediments: Comparison of Spectropotometric, Fluorometric, and High–Performance Liquid Chromatography Methods and Estimation of Detrital DNA, Applied and Environmental, Microbiology, 64:3238–3245 (1998).

Djordjevic et al. HPLC Separation of Oligonucleotides in Isocratic and Temperature–Programming Mode, Analytical Chemistry, 70:1921–1925 (1998).

Dole al et al. Micropreparative Separation of Transfer Ribonucleic Acids by High–Performance Liquid Chromatography, Journal of Chromatography, 463:409–417 (1989).

Drager et al. High–Performance Anion–Exchange Chromatpgraphy of Oligonucleotides, Analytical Biochemistry, 145:47–56 (1985).

Eder, P.S. et al. J Biol. Chemistry, Abstract, 266:6472–9(1991).

Garcia et al. Behaviour of Macromolecular RNA in Reversed–Phase HPLC, Journal of Chrom., Science, 21:398–404 (1983).

Georgopoulos et al. Use of High–Performance Liquid Chromatographic Fractionation by Large RNA Molecules in the Assay of Group I Intron Ribozyme Activity, Journal of Chrom. A, 868:109–114 (2000).

Goodwin et al. Studies on the Preparation and Characterisation of Monodisperse Polystyrene Latices, Colloid & Polymer Sci., 252: 464–471 (1974).

Green et al. HPLC Purification of Synthetic Oligodeoxyribonucleotides Containing Base—and Backbone–Modified Sequences, BioTechniques, 19:836–841 (1993).

Hirabayashi et al. Size–Dependent Chromatographic Separation of Double–Stranded DNA Which is Not Based on Gel Permeation Mode, Analytical Biochemistry, 178: 336–341 (1989).

Huber et al. Detection of Partial Denaturation in AT–Rich DNA Fragments by Ion–Pair Reversed–Phase Chromatography, Analytical Chemistry, 68:2959–2965 (1996).

Huber et al. A Comparison of Micropellicular Anion–Exchange and Reversed–Phase Stationary Phases for HPLC Analysis of Oligonucleotides, LC–GC 14:114–127 (1996).

Huber et al. High–Performance Liquid Chromatographic Separation of Detritylated Oligonucleotides on Highly Cross–Linked Poly(Sytrene–Divinylbenzene) Particles, Journal of Chromatography, 599:113–118 (1992).

Huber et al. Rapid and Accurate Sizing of DNA Fragments by Ion–Pair Chromatography on Alkylated Nonporous Poly-(Styrene–Divinylbenzene) Particles, Analytical Chemistry, 67:578–585 (1995).
Huber et al. High–Resolution Liquid Chromatography of DNA Fragments on Non–Porous Poly–Styrene–Divinylbenzene) Particles, Nucleic Acid Research, . 21:1061–1068 (1993).
Huber, et al. Rapid Analysis of Biopolymers on Modified Non–Porous Polystyrene–Divinylbenzene Particles, Chromatographia, 37:653–658 (1993).
Huber et al. High–Resolution Liquid Chromatography of Oligonucleotides on Nonporous Alkylated Styrene–Divinylbenzene Copolymers, Analytical Biochemistry, 212:351–358 (1993).
Ivanova, G.S. et al. Prikl Biokhim Mikrobiol, Abstract 11:746–51(1975).
Journal of Chromatography, Chromatography, 5th Edition, 51A:A299–A300 (1992).
Jünemann et al. In Vivo Deuteration of Transfer RNAs: Overexpression and Large–Scale Purification of Deuterated Specific tRNAs, Nucleic Acids Research, Oxford University Press, No. 5, 24:907–913, 1996.
Kanduc, Fractionation of Rat Liver tRNA by Reversed–Phase High Performance Liquid Chromatography: Isolation of ISO–tRNAs, Preparative Biochemistry, 24:167–174 (1994).
Kato et al. Separation of DNA Restriction Fragments by High–Performance Ion–Exchange Chromatography on a Non–Porous Ion Exchanger, Journal of Chromatography, 478: 264–268 (1989).
Klink et al. Contribution of Disulfide Bonds to the Conformational Stability and Catalytic Activity of Ribonuclease A, Eur. J. Biochem. 267:566–572 (2000).
Kwiatkowski, M. et al. Acta Chemica Scandinavica, 4:1–13 (1984).
Lalioti et al. Purification and Characterization of a Novel Poly (U), Poly (C) Ribonuclease From *Saccharomyces cerevisiae*, Biochimica et Biophysica Acta 1342:62–72 (1997).
Lehninger, Principles of Biochemistry, Worth Publishers, pp. 874–876 (1982).
Matsumura et al. Enormously Fast RNA Hydrolysis by Lanthanide (III) Ions Under Physiological Conditions: Eminent Candidates for Novel Tools of Biotechnology, J. Biochem., 122:387–394 (1997).
Matthews et al. Analytical Strategies for the Use of DNA Probes, Analytical Biochemistry, 169, 1–25, Feb., 1988.
McFarland et al. Separation of Oligo–RNA by Reverse–Phase HPLC, Nucleic Acids Research, No. 4, 7:1067–1080 (1978).
Oefner, Peter J. et al. Research Reports 16:1–8(1994).
Oefner, Peter J. et al. Analytical Biochemistry, 223:001–008(1994).
Oefner et al. High–Resolution Liquid Chromatography of Nucleic Acids, American Laboratory, 26:28C–28J (1994).

Ohgi, K. et al. J. Biochemistry (Tokyo), Abstract 94:767–75(1983).
Ohmiya et al. Anal. Biochem., 189:126–130 (1990).
Pager, A Liquid Chromatpgraphic Prepartion of Retroviral RNA, Anal. Biochem., 215:231–235 (1993).
Petro et al. Molded Monolithic Rod of Macroprous Poly (Styrene–Co–Divinylbenzene) as a Separation Medium for HPLC of Synthetic Polymers . . . , Analytical Chemistry, 68:315–321 (1996).
Promega, RNA Applications Guide, Chapters 1 (Prevention of RNA Degradation) and 2 (RNA Purification), downloaded from *http://www.promega.com* on Jun. 4, 2001.
Qiagen, RNA/DNA Handbook, *http://www.qiagen.com* (1998).
Qiagen, RNeasy© Midi/Maxi Handbook, *http://www.qiagen.com* (1999).
Qiagen, RNeasy© Protect and RNAlater™ Handbook, *http://www.qiagen.com* (2000).
Rauhut et al. mRNA Degradation in Bacteria, FEMS Microbiology Reviews, 23:353–370 (1999).
Robinson et al. Quantification of Alternatively Spliced Rush mRNA Insoforma by QRT–PCR and IP–RP–HPLC Analysis: A New Approach to Measuring Regulated Splicing Efficiency, Gene, 198:1–4 (1997).
Sambrook, J. et al. Cold Spring Harbor Laboratory Press, $2^{nd}$ Edition, 7.2–7.5(1989).
Serra et al. Predicting Thermodnamic Properties of RNA, Methods in Enzymology, pp. 242–255 (1987).
Snyder et al. Gradient Elution in Reversed–Phase HPLC, Anal. Chem., No. 14, 55:1412A–1430A (1983).
Sugimoto et al. Experimental Quantitation of Cation Effect on Nucleic Acid Stability, Nucleic Acids Symposium Series, 37:147–148 (1997).
Tanaka et al. High Resolution Chromatography of Ribonucleosides and its Application to RNA Analysis, Biomedical Chromatography, vol. 3, No. 6, (1989).
Uchida, T. et al. J. Biochemistry (Tokyo), Abstract, 90:463–71(1981).
Ugelstad et al. Swelling of Oligomer–Polymer Particles. New Methods of Preparation of Emulsions and Polymer Dispersions, Advances in Colloid and Interface Science, 13:101–140 (1980).
Van Der Mast, C.A., et al. Separation of translationally active mRNAs by reversed–phase ion–pair high–performance liquid chromatography, Journal of Chromatography, Chrombio 5675, 564:115–125 (1991).
Wang et al. Reversed–Phase Chromatography of Small Molecules and Peptides on a Continous Rod of Macroporous Poly(Styrene–Codivinylbenzene), Journal of Chromatography, 669:230–235 (1994).
Wincott et al., Synthess, Deprotection, Analysis and Purification of RNA and Robozymes, Nucleic Acids Research, No. 14, 23:2677–2684 (1995).
Yasuda, T. et al. Am. J. Hum. Genetics, Abstract, 42:608–14(1988).

LOAD

INJECT

LOAD

INJECT

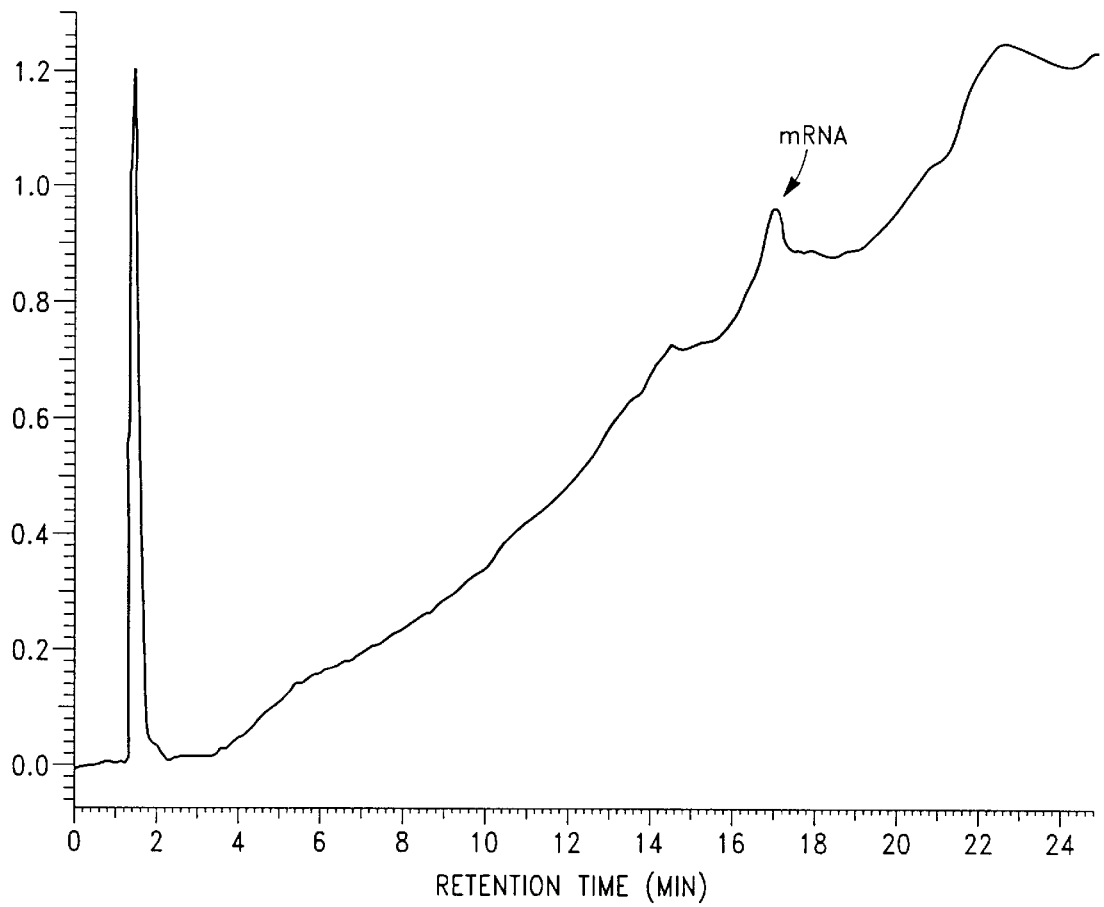
FIG.—19
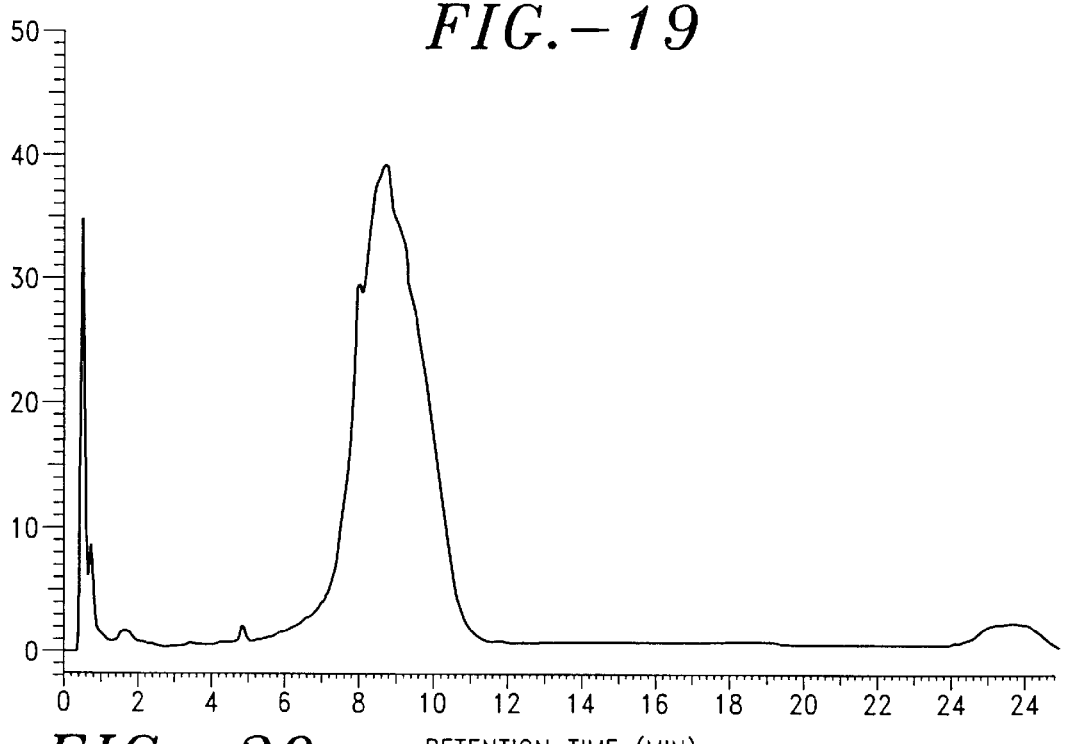
FIG.—20

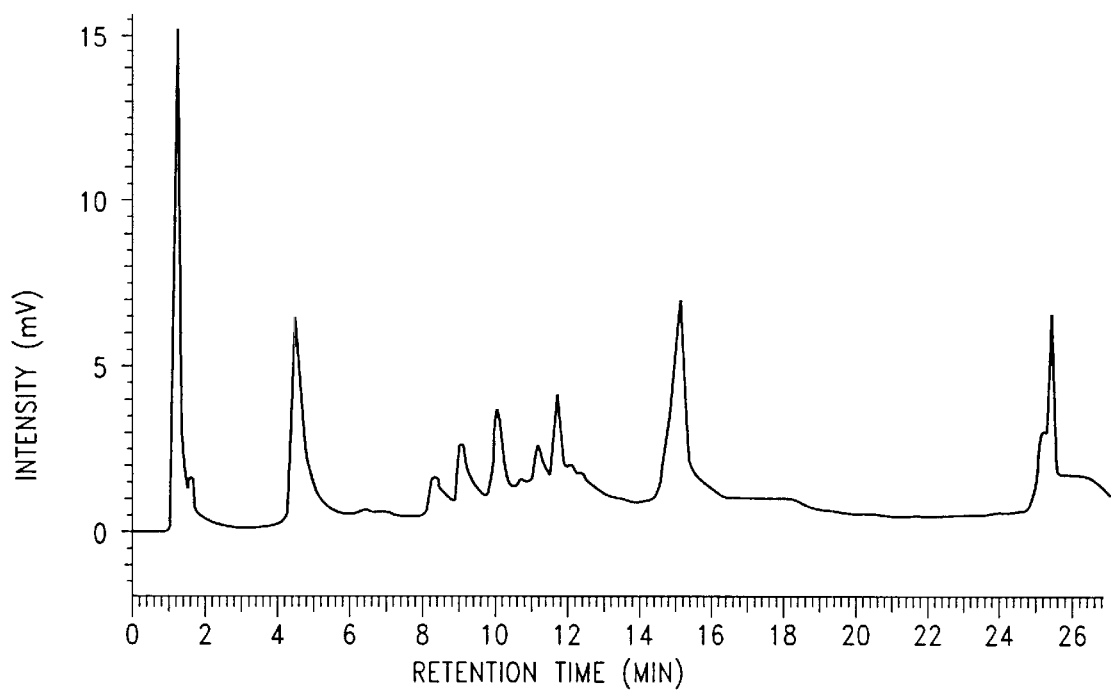
FIG.—23
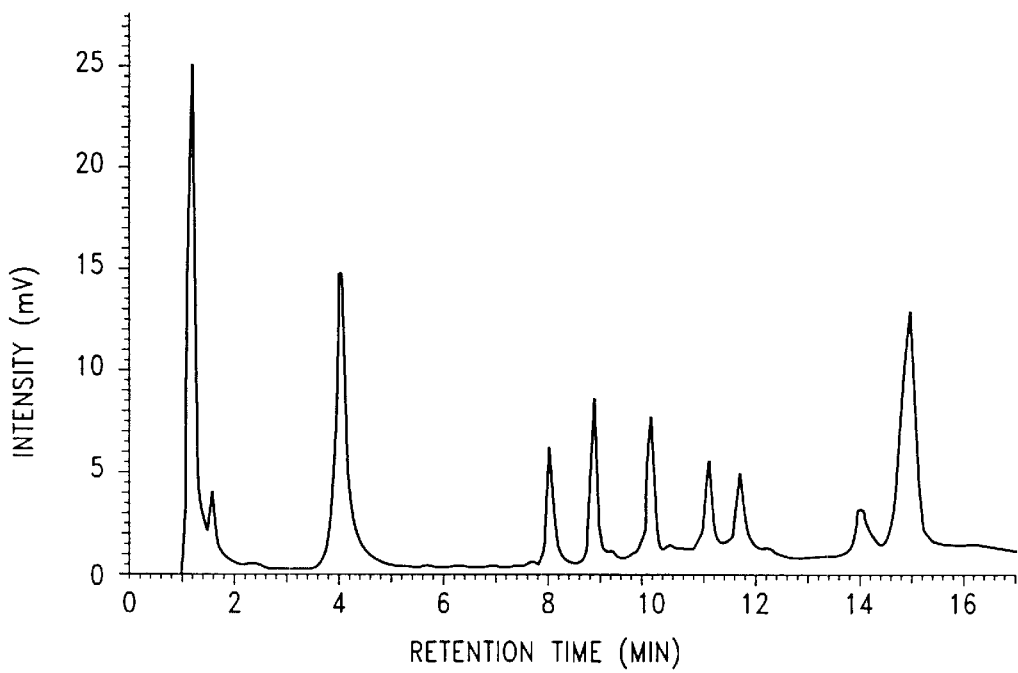
FIG.—24

METHOD AND SYSTEM FOR RNA ANALYSIS BY MATCHED ION POLYNUCLEOTIDE CHROMATOGRAPHY

CROSS REFERENCE TO RELATED APPLICATIONS

This application is a continuation in part of U.S. patent application Ser. No. 09/557,424 filed Apr. 21, 2000, now U.S. Pat. No. 6,475,388, which is a continuation in part of U.S. patent application Ser. No. 09/183,123 filed Oct. 30, 1998 (now U.S. Pat. No. 6,066,258), which is a continuation in part of U.S. patent application Ser. No. 09/058,580 filed Apr. 10, 1998 (abandoned), which is a continuation in part of U.S. patent application Ser. No. 08/748,376 filed Nov. 13, 1996 (now U.S. Pat. No. 5,772,889). This application is a regular U.S. patent application under 35 U.S.C. §111(a) and 35 U.S.C. §1.53(b) and claims priority from the following co-pending, commonly assigned provisional applications, each filed under 35 U.S.C. §111(b), each of which is incorporated herein by reference:

60/187,979 filed Mar. 9, 2000

60/224,918 filed Aug. 11, 2000;

60/215,208 filed Jun. 29, 2000;

60/220,119 filed Jul. 21, 2000.

FIELD OF THE INVENTION

The present invention is directed to the analysis of RNA molecules by liquid chromatography. More specifically, the invention is directed to a liquid chromatography system and method, such as Matched Ion Polynucleotide Chromatography, which enhances the purification of RNA.

BACKGROUND OF THE INVENTION

RNA molecules are polymers comprising sub-units called ribonucleotides. The four ribonucleotides found in RNA comprise a common cyclic sugar, ribose, which is covalently bonded to any of the four bases, adenine (a purine), guanine (a purine), cytosine (a pyrimidine), and uracil (a pyrimidine), referred to herein as A, G, C, and U respectively. A variety of modified bases are also encountered in RNA. A phosphate group links a 3'-hydroxyl of one ribonucleotide with the 5'-hydroxyl of another ribonucleotide to form a polymeric chain. Secondary structure commonly occurs via intra-chain hydrogen bonds between complementary bases.

Ribonucleic acid (RNA) transports genetic information within the cell. In the most general terms, RNA passes specific peptide and protein coding information from the genome in the nucleus to those parts of the cell responsible for the production of these peptides and proteins. There are a number of different RNAs found in the cell at any given time. Some of them are noted below, along with their functions:

Messenger RNA (mRNA): Carries the coding messages to the ribosomes for the production of peptides and proteins;

Small nuclear RNA (snRNA): Responsible for removing intronic sequences from mRNA precursors (preribosomal mRNAs), prior to the spliced mRNA delivery to the ribosomes;

Transfer RNA (tRNA): Provide chemically activated amino acids for binding to the ribosomal complex in the process of protein synthesis;

Ribosomal RNA (rRNA): RNA within the ribosomes themselves, which by association, are part of the protein synthesis process.

Within molecular biology, it is often necessary to isolate these RNA molecules, particularly mRNA. This is because an mRNA "message" indicates that a gene has been transcribed. Furthermore, the extent to which the gene is expressed (up-regulated, down-regulated, turned on, turned off) is often proportional to the amount of gene-specific RNA (mRNA) present in the cell. The quantitation of gene expression via mRNA content can occur by various means (e.g., RT-PCR, expression array/hybridization analysis, etc.)

On other occasions it is desirable to create a compilation, or "library", of those genetic messages being expressed in a cell or cells under a given set of conditions (i.e., normal vs. diseased state). This is often performed by selectively harvesting the mRNAs present in a sample, reverse transcribing the mRNAs to cDNA (first strands and second strands), and then cloning these double stranded sequences into some suitable vector. Once cloned, the cDNA "libraries" can be utilized in various procedures.

RNA is thus the starting material in numerous molecular biology experiments involving the identification of unknown genes and assignment of functions to various proteins. Quality, quantity, purity, and size distribution of RNA determine the rate of success in applications such as cDNA library construction, Northern blot analysis, reverse transcription, and in situ analysis. Present techniques for the purification of RNA are labor intensive and lengthy. Quantification is routinely performed by gel visualization, radiometric methods, and spectrophotometric techniques. Sizing and quality determination is often performed by electrophoresis on denaturing agarose gels. However, RNA can become covalently modified by the chemicals used during the fractionation process (e.g., formaldehyde or acryalmide). Many of the present separation techniques require the use of hazardous chemicals (e.g., methylmercuric hydroxide, CsCl) such as described in *Current Protocols in Molecular Biology*, F. M. Ausubel et al. (1995) Eds., John Wiley & Sons, pp. 4.0.1–4.10.11 and in J. Sambrook et al. (1989) *Molecular Cloning: A Laboratory Manual*, Second Edition, Cold Spring Harbor Laboratory Press, New York.

In the preparation of mRNA from total RNA, spin columns containing beads coated with poly T oligomers are often used (e.g., Poly(A)Pure™ mRNA Purification Kit, Ambion, Inc., Austin, Tex.; Oligotex™ mRNA Purification System, Qiagen, Inc., Valencia, Calif.). The disadvantages of this technique include a requirement for high amounts of total RNA sample due to low recovery of mRNA, contamination of the product (e.g. by rRNA), and degradation of the mRNA product.

There is a need for faster, safer, more reliable, less labor intensive, and more accurate methods of RNA analysis.

Separations of polynucleotides such as RNA have been traditionally performed using electrophoresis through agarose gels or sedimentation through sucrose gradients. However, liquid chromatographic analysis of polynucleotides is becoming more important because of the ability to automate the process and to collect fractions.

Traditional chromatography is a separation process based on partitioning of mixture components between a "stationary phase" and a "mobile phase". The stationary phase is provided by the surface of solid materials which can comprise many different materials in the form of particles or passageway surfaces of cellulose, silica gel, coated silica gel, polymer beads, polysaccharides, and the like. These materials can be supported on solid surfaces such as on glass plates or packed in a column. The mobile phase can be a liquid or a gas in gas chromatography.

The separation principles are generally the same regardless of the materials used, the form of the materials, or the apparatus used. The different components of a mixture have different respective degrees of solubility in the stationary phase and in the mobile phase. Therefore, as the mobile phase flows over the stationary phase, there is an equilibrium in which the sample components are partitioned between the stationary phase and the mobile phase. As the mobile phase passes through the column, the equilibrium is constantly shifted in favor of the mobile phase. This occurs because the equilibrium mixture, at any time, sees fresh mobile phase and partitions into the fresh mobile phase. As the mobile phase is carried down the column, the mobile phase sees fresh stationary phase and partitions into the stationary phase. Eventually, at the end of the column, there is no more stationary phase and the sample simply leaves the column in the mobile phase.

A separation of a mixture of components occurs because the mixture components have slightly different affinities for the stationary phase and/or solubilities in the mobile phase, and therefore have different partition equilibrium values. Therefore, the mixture components pass down the column at different rates.

In traditional liquid chromatography, a glass column is packed with stationary phase particles and mobile phase passes through the column, pulled only by gravity. However, when smaller stationary phase particles are used in the column, the pull of gravity alone is insufficient to cause the mobile phase to flow through the column. Instead, pressure must be applied. However, glass columns can only withstand about 200 psi. Passing a mobile phase through a column packed with 5 micron particles requires a pressure of about 2000 psi or more to be applied to the column. 5 to 10 micron particles are standard today. Particles smaller than 5 microns are used for especially difficult separations or certain special cases). This process is denoted by the term "high pressure liquid chromatography" or HPLC.

HPLC has enabled the use of a far greater variety of types of particles used to separate a greater variety of chemical structures than was possible with large particle gravity columns. The separation principle, however, is still the same.

An HPLC-based ion pairing chromatographic method was recently introduced to effectively separate mixtures of polynucleotides wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). Ion pair reverse phase high pressure liquid chromatography (IPRPHPLC) was used as a process for separating DNA using non-polar separation media, wherein the process used a counterion agent, and an organic solvent to release the DNA from the separation media. This method was used in the separation of double stranded and single stranded DNA.

SUMMARY OF THE INVENTION

Objects of the present invention include providing a method and system for segregating RNA molecules which is fast, safe, reliable, convenient, reproducible, and quantitative.

In one aspect, the invention provides a chromatographic method for segregating a mixture of RNA molecules. The method includes applying the mixture to a polymeric separation medium having non-polar surfaces, and eluting said RNA molecules with a mobile phase which includes counterion reagent and an organic component. The preferred surfaces are characterized by being substantially free from multivalent cations which are free to interfere with RNA segregation. The elution of the RNA molecules is preferably carried out at a minimum denaturing temperature. For example, the elution can be carried out at a temperature greater than about 60° C. Preferably, the elution is carried out at a temperature within the range of about 60° C. to about 100° C. The pH of the mobile phase is preferably within the range of about pH 5 to about pH 9. The method is useful in the segregation of RNA molecules exceeding about 1,000 nucleotides and can be used in the segregation of RNA molecules having up to about 20,000 nucleotides.

In the method, the segregation can be performed using a column containing polymeric beads having non-polar surfaces, wherein the beads have an average diameter of about 1 to about 100 microns. The separation medium can include polymer beads having an average diameter of 0.5 to 100 microns, the non-polar surfaces being unsubstituted or having bound thereto a hydrocarbon group having from 1 to 1,000,000 carbons.

The separation can be performed using a column including a polymeric monolith. The surfaces of the monolith can be unsubstituted or substituted with a hydrocarbon group having from 1 to 1,000,000 carbons. The monolith can include monovinyl substituted aromatic compound, divinyl substituted aromatic compound, acrylate, methacrylate, polyolefin, polyester, polyurethane, polyamide, polycarbonate, fluoro-substituted ethylene, or combinations of one or more thereof.

The method can include collecting mobile phase fractions containing the RNA molecules. The method can include detecting RNA molecules (e.g. using UV detection) during the elution step. The segregating is preferably performed by Matched Ion Polynucleotide Chromatography. The mobile phase preferably includes a counterion agent and an organic solvent, wherein the organic solvent is water soluble.

Examples of multivalent metal cations that can interfere with the segregation include Fe(III), Cu(II), Cr(III), and colloidal metal. During the elution, the mobile phase can include a multivalent cation binding agent such as EDTA.

Examples of an organic solvent useful in the method include alcohol, acetonitrile, dimethylformamide, tetrahydrofuran, ester, ether, or mixtures of one or more thereof. In the method, the counterion agent can be selected from lower alkyl primary amine, lower alkyl secondary amine, lower alkyl tertiary amine, lower trialkyammonium salt, quaternary ammonium salt, or mixtures of one or more thereof. Non-limiting examples of preferred counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, triethylammonium hexafluoroisopropyl alcohol, or mixtures of one or more thereof.

In the method, the separation medium can be subjected to a prior acid wash treatment to remove any residual metal contaminants. In the method, the separation medium can be subjected to a prior treatment with multivalent cation binding agent.

In another aspect, the invention provides a chromatographic method for segregating a mixture of RNA molecules having lengths exceeding about 100 nucleotides. The method includes (a) flowing the mixture through a separation column containing polymer beads having an average diameter of 0.5 to 100 microns, the beads being unsubstituted polymer beads or polymer beads substituted with a moiety selected from the group consisting of hydrocarbon having from 1 to 1,000,000 carbons, and (b) segregating the mixture of RNA molecules at a minimum denaturing temperature.

In yet another aspect, the invention provides a chromatographic method for segregating a mixture of RNA molecules. The method includes (a) flowing the mixture through a separation column containing polymer beads having an average diameter of 0.5 to 100 microns, the beads being unsubstituted polymer beads or polymer beads substituted with a moiety selected from the group consisting of hydrocarbon having from 1 to 1,000,000 carbons. The preferred beads are characterized by being substantially free from multivalent cations which are free to bind with said RNA, (b) segregating said mixture of RNA molecules at a minimum denaturing temperature.

In a further aspect, the invention includes an improved method for segregating a mixture of RNA molecules by Matched Ion Polynucleotide Chromatography, said mixture comprising molecules having lengths exceeding about 100 nucleotides. The method includes (a) applying a solution of the molecules and counterion reagent to a column containing polymeric separation beads having non-polar surfaces, wherein the separation beads have an average diameter of 1 to 100 microns, the column having an ID greater than about 5 mm and (b) eluting the RNA molecules with a mobile phase which includes the counterion reagent and an organic component. The method can be carried out at a temperature within the range of about 60° C. to about 90° C. The ID can be greater than about 7 mm. The ID can be greater than about 10 mm. The ID is preferably within the range of about 5 mm to about 1 m.

In still another aspect, the instant invention concerns an improved reverse phase chromatography column for segregating a mixture of RNA molecules by Matched Ion Polynucleotide Chromatography, the mixture comprising molecules having lengths exceeding about 100 nucleotides. The improved column includes a cylinder containing polymer beads, the beads having an average diameter of 1 to 100 microns, the beads being unsubstituted polymer beads or polymer beads substituted with a hydrocarbon moiety having from 1 to 1,000,000 carbons, the column having an ID greater than about 5 mm.

In a yet further aspect, the invention concerns a chromatography system for segregating a mixture of RNA molecules by Matched Ion Polynucleotide Chromatography which includes a cylindrical column containing polymer beads, the beads having an average diameter of 1 to 100 microns, the beads being unsubstituted polymer beads or polymer beads substituted with a hydrocarbon moiety having from 1 to 1,000,000 carbons, the column having an ID greater than about 5 mm.

In a further aspect, the invention provides a chromatographic method for segregating a mixture of RNA molecules having lengths exceeding about 100 nucleotides. The method includes (a) applying a solution of the fragments and counterion reagent to a column containing polymeric beads having non-polar surfaces, wherein the beads have an average diameter of about 1 to about 100 microns, wherein the surfaces are characterized by being substantially free from multivalent cations which are free to bind with the RNA and (b) eluting the RNA molecules with a mobile phase which includes said counterion reagent and an organic component. The eluting can be carried out at a minimum denaturing temperature.

BRIEF DESCRIPTION OF THE DRAWINGS

FIG. 19 is a chromatogram from a MIPC analysis of RNA from a plant extract after a second affinity purification.

FIG. 20 is a chromatogram from a MIPC analysis of mouse brain mRNA.

FIG. 23 illustrates an elution profile from MIPC analysis of RNA size markers carried out at a column temperature of 40° C.

FIG. 24 illustrates an elution profile from MIPC analysis of RNA size markers carried out at a column temperature of 50° C.

DETAILED DESCRIPTION OF THE INVENTION

Figure 1:
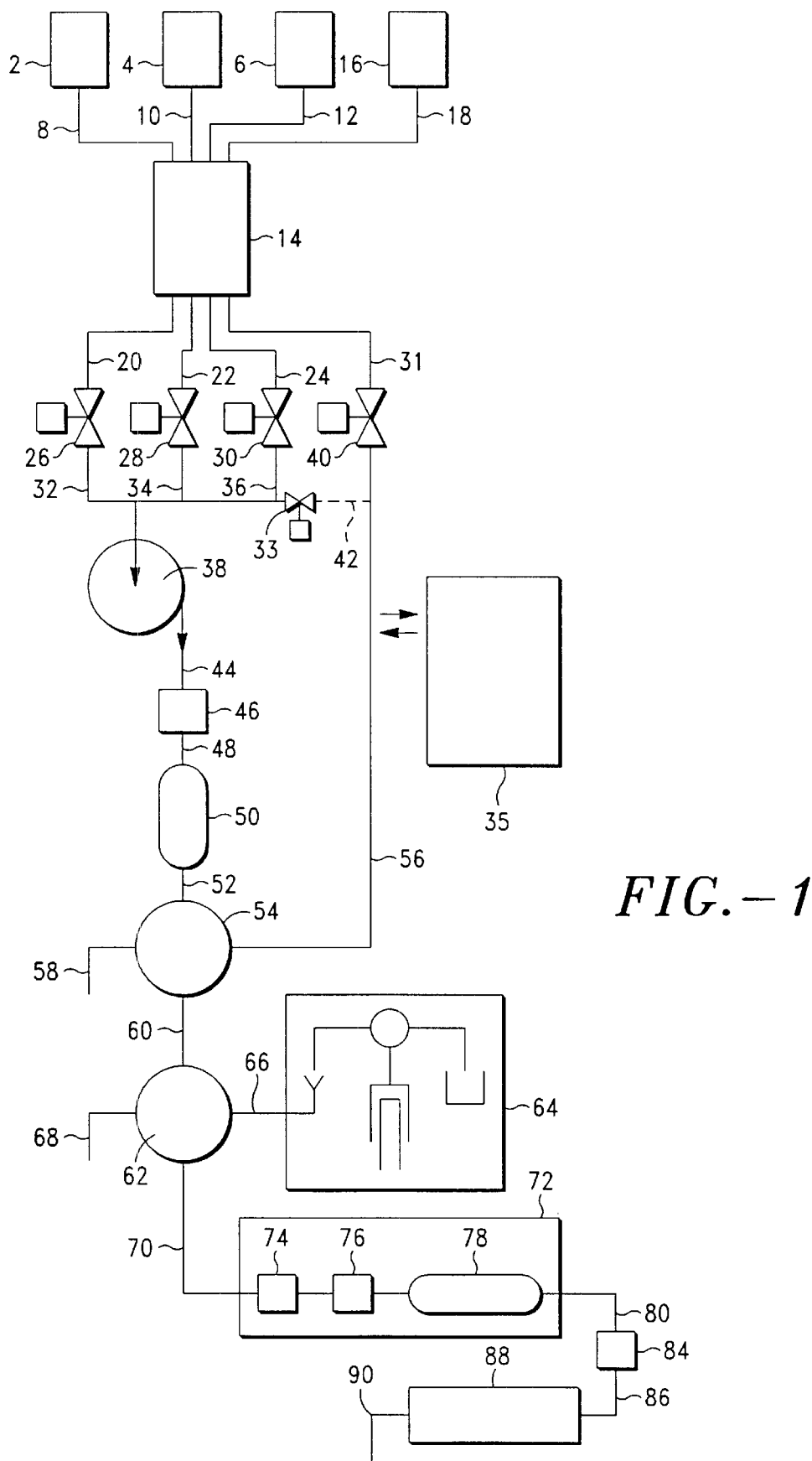
FIG. 1 is a schematic representation of a single column MIPC system using valves and valve controls to establish mobile phase gradients.

In one aspect, the present invention concerns a Matched Ion Polynucleotide Chromatography (MIPC) method and system for segregating a mixture of RNA molecules.

"Matched Ion Polynucleotide Chromatography" as defined herein, includes a process for segregating RNA molecules using non-polar reverse phase media, wherein the process uses a counterion agent, and an organic solvent to release the RNA molecules from the reverse phase media.

"Segregating" as defined herein includes a Matched Ion Polynucleotide Chromatography process for separating RNA molecules in which the retention time of a molecule is primarily based on nucleotide length but in which the retention time can be subject to bias due to the influence of the polarity of the bases. The bias can either increase or decrease the retention time.

In its most general form, the subject matter of the present invention concerns the segregation of RNA molecules utilizing a stationary separation medium having non-polar surfaces. The preferred surfaces are substantially free from multivalent cations which are free to bind with the RNA molecules. The segregation is performed on the stationary surface. The surface can be porous, but preferably any surface pores are of a size which excludes the smallest RNA molecule being analyzed.

The medium can be enclosed in a column. In one embodiment, the non-polar surfaces comprise the surfaces of polymeric beads. In an alternative embodiment, the surfaces comprise the surfaces of interstitial spaces in a molded polymeric monolith. For purposes of simplifying the description of the invention and not by way of limitation, the segregation of RNA molecules using nonporous beads, and the preparation of such beads, will be primarily described herein, it being understood that other separation surfaces, such as the interstitial surfaces of polymeric monoliths, are intended to be included within the scope of this invention. Monoliths, such as rods, contain polymer separation media which have been formed inside a column as a unitary structure having through pores or interstitial spaces which allow eluting mobile phase and analyte to pass through and which provide the non-polar separation surface.

In general, the only requirement for the separation media of the present invention is that they must have a surface that is either intrinsically non-polar or be bonded with a material that forms a surface having sufficient non-polarity to interact with a counterion agent.

In one aspect, the subject matter of the present invention is the segregation of RNA molecules utilizing columns filled with nonporous polymeric beads having an average diameter of about 0.5–100 microns; preferably, 1–10 microns; more preferably, 1–5 microns. Beads having an average diameter of 1.0–3.0 microns are most preferred.

Embodiments of the MIPC process are disclosed in earlier, co-pending and commonly assigned U.S. Patents or Patent Applications: U.S. Pat. Nos. 5,772,889; 5,997,742; 5,972,222; 5,986,085; 6,017,457; 6,030,527; 6,056,877; 6,066,258; 6,136,195; U.S. patent application Ser. Nos. 09/058,580 filed Apr. 10, 1998 (abandoned); 09/129,105 filed Aug. 4, 1998; 09/169,440 filed Oct. 9, 1998; 09/318,407 filed May 25, 1999; 09/469,551 filed Dec. 22, 1999; 09/557,424 filed Mar. 21, 2000; 09/548,983 filed Apr. 14, 2000; and 09/562,069 filed May 1, 2000, each of which patents or patent applications is incorporated by reference in its entirety herein.

RNA molecules often include intramolecular hydrogen bonds between bases. Intramolecular hydrogen bonds contribute to the secondary structure of RNA (see Lehninger, Principles of Biochemistry pp. 874–876 (Worth Publishers, 1982)).

The term "secondary structure" refers to the manner in which successive bases of a polynucleotide are arranged in space. The secondary structure results from hydrogen bonding patterns between bases. For example, single-stranded RNA molecules often poses such intramolecular hydrogen bonding patterns. An example of such a structure includes a haripin loop.

The "minimum denaturing temperature" is defined herein to include a temperate sufficient for fully denaturing all intramolecular hydrogen bonds between bases in an RNA molecule.

The "separation temperature" includes reference to the temperature of the separation medium and of the mobile phase in contact with the separation medium. In the present invention, it is assumed that the column oven heats both the separation medium and the mobile phase flowing through the separation medium to about the same temperature.

The preferred MIPC system provides automated options for sample selection, mobile phase gradient selection and control, column and mobile phase temperature control, and fraction collection.

FIG. 1 is a schematic layout of the system in accordance with one embodiment of the MIPC system. A plurality of containers can be used as reservoirs for solutions, such as solvents, counterions, and other solutions, which make up the mobile phase. For example, container 2 can contain an aqueous component of a mobile phase such as an aqueous solution of counterion agent (e.g., triethylammonium acetate (TEAA)), and container 4 can contain an aqueous solution of counterion agent plus organic (driving) solvent (e.g., TEAA plus acetonitrile). An auxiliary liquid (e.g., a co-solvent) can be held in container 6. These solutions are mixed to achieve a selected concentration of organic solvent in the mobile phase during a separation. Other examples of these solutions are provided in the Examples herein and in the commonly assigned patent indicated hereinabove. The containers have respective transport tubing such as counterion solution transport tubing 8, solvent solution transport tubing 10, and auxiliary liquid transport tubing 12 communicating therewith, and leading to degasser 14.

The degasser 14 removes dissolved gases from the liquids. An example of a suitable degasser is the Degassit Model 6324. Removal of dissolved oxygen is particularly important because its presence increases the risk of oxidizing ferrous or other oxidizable metals in the system components and thus introducing the corresponding cations into the mobile phase liquid.

Figure 2:
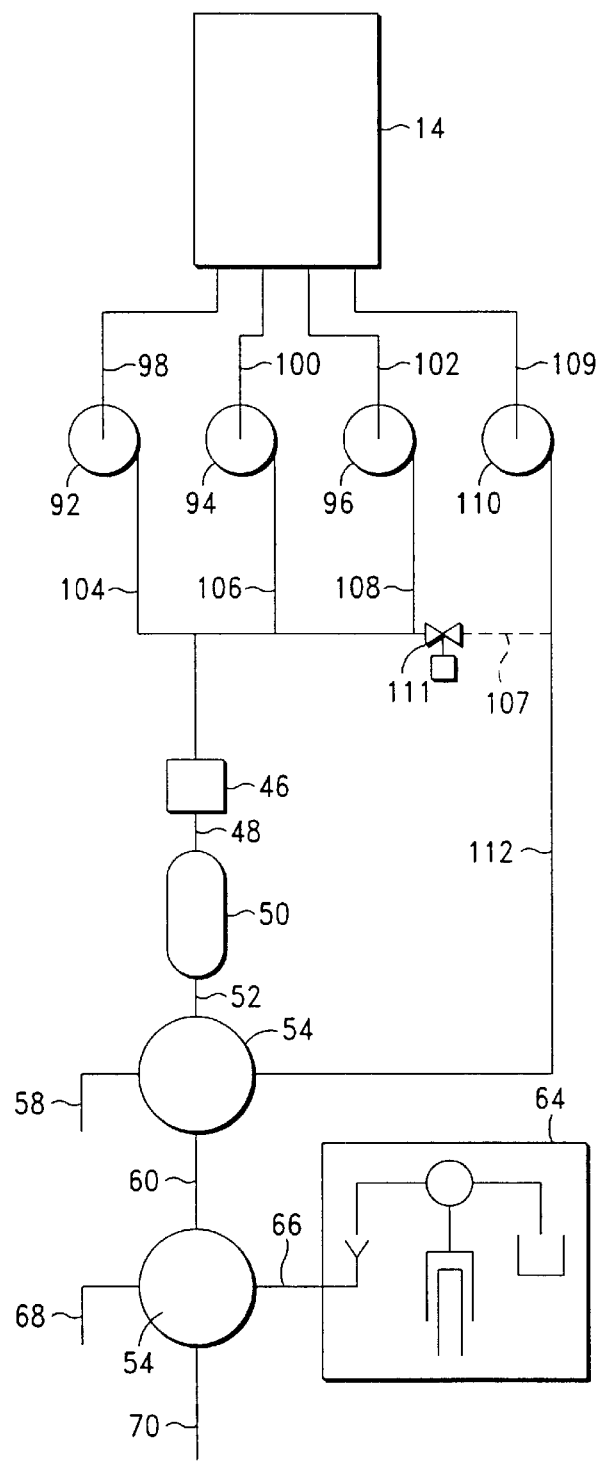
FIG. 2 is a partial schematic representation of a pump system for establishing mobile phase gradients.

Column cleaning solution is contained in cleaning solution container 16 which likewise has a cleaning solution transport conduit 18 communicating therewith leading to the degasser 14. In this embodiment, the cleaning solution can flow by gravity pressure if the container 16 is elevated above the degasser and injection valve 54. Alternatively, a pump 110 as shown in FIG. 2 can be provided to achieve cleaning solution flow.

The system of the invention incorporates conventional mobile phase flow control means which controls flow of solvent solution and aqueous components of a mobile phase. In one embodiment, the mobile phase flow control means comprises a set of flow control valves, each with automatic opening controls under computer control as described hereinbelow. In another embodiment the mobile phase flow control means comprises a set of pumps, the flow setting of which are responsive to computer control as described hereinbelow The system illustrated in FIG. 1 utilizes one embodiment of a mobile phase flow control means which includes a set of flow control valves. Degassed counterion solution conduit 20, degassed solvent solution conduit 22, and degassed auxiliary liquid conduit 24 leading from the degasser 14 communicate with respective aqueous component proportioning valve 26, solvent solution proportioning valve 28, and auxiliary liquid proportioning valve 30. The settings for these proportioning valves are set and changed by valve operators such as stepper motors associated therewith, and these valve operators respond to establish a desired set of settings in response to commands from the mobile phase flow control software module described in greater detail hereinbelow. The flow control valves 26, 28, and 30 comprise an embodiment of a mobile phase flow control means which controls the flow of solvent solution and other components of the mobile phase. The settings for these valves control the ratio of liquids (co-solvents, solvent solution, etc.) through the injector valve and the separation column. Conduits 32, 34, and 36 lead from respective proportioning valves 26, 28 and 30 to the intake of pump 38.

The cleaning solution transport conduit 31 leads to a cleaning solution valve 40. An optional cleaning solution conduit 42 leads from the valve 40 and communicates with the inlet of pump 38. Valve 33 controls flow through conduit 42.

The openings of valves 26, 28 and 30 accurately set the relative ratios of the organic solvent, and other components, within the mobile phase, a most important part of this system because the RNA segregation by MIPC is a function of solvent concentration. As will be described in regard to the various RNA segregation processes, the slope of the organic solvent gradient as a function of time is changed during the separation process, and the most critical phase may require a very precise gradient. The settings of the valves 26, 28 and 30 are established by conventional valve actuators which can be remotely set by signals to a conventional valve control device.

In a preferred embodiment, the separation system is under computer control as represented at 35. The computer includes Instrument Control Software which provides computer controlled instructions for establishing the settings of valves 26, 28 and 30 to precise flow values at appropriate times during the operation of the system.

In a similar manner, the Instrument Control Software of the instant invention provides computer controlled instructions to establish the operational parameters of the pump 38, such as the off/on status of the pump and the pressure or flow rate settings of the pump.

Pump outflow conduit 44 communicates with the in-line mixer 46, directing the liquid flow through the mixer 46 for thorough mixing of the components. Mixed liquid outflow conduit 48 communicates with optional guard column 50 to treat the mixed liquid to remove multivalent metal cations and other contaminants which would interfere with the segregation of RNA molecules. Guard column 50 can contain a cation exchange resin in sodium or hydrogen form for removal of multivalent metal cations by conventional ion exchange. Conduit 52 communicates with the outlet of the guard column and an inlet port of a cleaning solution injector valve 54. Cleaning solution supply conduit 56 connects valve 40 with the cleaning solution injector valve 54, and waste outlet conduit 58 leads to waste. Conduit 60 leads from valve 54 to the sample injection valve 62.

Sample aliquot selector 64 communicates with injector valve 62 through sample conduit 66. Waste conduit 68 leads from the injector valve and removes waste liquids.

In the injector valve 62, the sample is introduced into a stream of solvent and carrier liquid passing through the valve from conduit 60. Sample conduit 70 communicates with an outlet port of injector valve 62 and with the column prefilter 74 in the air bath oven 72. The capillary tubing coil 76 communicates with the prefilter 74 and the inlet of chromatography column 78. The extended length of the capillary coil 76 allows ample heat to pass from the heated oven air into the liquid passing through the coil, bringing the liquid within ±0.05° C. of a selected temperature. The oven 72 establishes this temperature uniformity in the prefilter 74, coil 76, and chromatography column 78.

The separation column 78 is packed with beads having a unique separation surface which effects segregation of RNA molecules in the presence of a counterion by the MICP process. The segregation process and details about the column and beads are described in detail hereinbelow. A stream of mobile phase containing segregated RNA molecules passes from the chromatography column 78 through conduit 80.

Conduit 80 communicates with a detector 84. The detector can be a conventional UV absorbance device which measures the UV absorbance of the RNA fragment structures in the liquid mobile phase. The absorbance is a function of the concentration of the RNA fragments in the liquid being tested.

Alternatively, if the RNA is labeled with a fluorescent marker, the detector can be a fluorescence detector which can continuously measure the level of the fluorescent =marker in the liquid by detecting the emission level at the frequency most appropriate for the marker. It will be readily apparent that any detecting system capable of continuously measuring a characteristic of the liquid which is a function of the concentration of the RNA molecules therein is suitable and intended to be within the scope of this invention. Examples of suitable detectors include the L-7420 UV-Vis detector, and the L-7480 Fluorescence detector available from Hitachi. The electrical output from the detector preferably is converted to a digital form by an A/D converter and recorded in standard digital format to a digital storage device such as a disk drive in computer 35. Conduit 86 removes the tested liquid. The mobile phase then passes to the automated fraction collector 88 where selected portions of the mobile phase fractions are collected in vials for later processing or analysis. Uncollected fractions are removed through conduit 90.

In the above description, the liquid flow system is described as a series of conduits. The conduits are capillary tubing selected to avoid introduction of multivalent cations into the liquids. The preferred capillary tubing materials are titanium and PEEK. The other components of the system are preferably made of titanium or PEEK or have the surfaces exposed to the liquid coated with PEEK to protect them from oxidation and prevent the introduction of multivalent cations into the liquid. Stainless steel can also be used but is preferably treated to remove all oxidized surface materials and the solutions contacting the stainless steel surfaces are free of dissolved oxygen.

Illustrating another embodiment of a mobile phase flow control means, FIG. 2 is a partial schematic representation of a pump system for establishing mobile phase composition. This system relies on proportioning pumps to control the ratio of aqueous component and solvent solution, such as solutions A and B described hereinabove. The inlets of proportioning pumps 92, 94 and 96 by way of their respective supply conduits 98, 100, and 102 communicate with the degasser 14, and by way of their respective outlet conduits 104, 106 and 108 communicate with the inline mixer 46. The operational speed for these proportioning pumps are calibrated to flow rates therethrough and are controlled by a flow control software module described in greater detail hereinbelow. The settings for these proportioning valves control the liquid flow speed and the ratio of liquids (co-solvents, driving solvents, etc.) through the injector valve and the separation column.

A pump 110 can supply cleaning solution to the system through optional conduit 112. An optional conduit 107 leads from conduit 112 and communicates with the in-line mixer 46. Valve 111 controls flow through conduit 107.

Examples of suitable mobile phase control means for use in the invention include the programmable dual piston pump Model L-7100 available from Hitachi and the Model 2690 Separations Module available from Waters.

Figure 3:
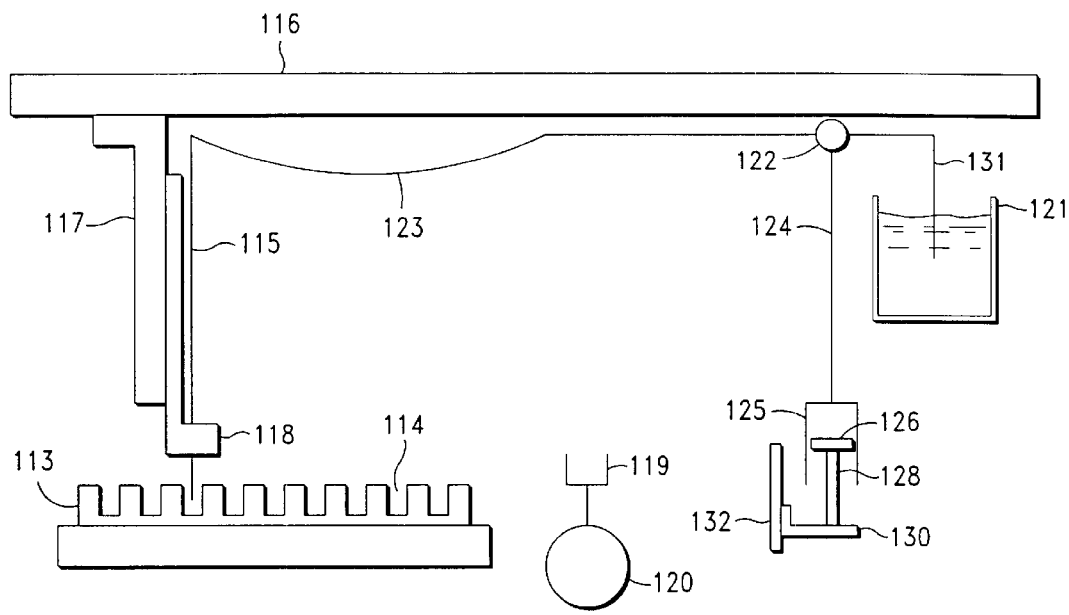
FIG. 3 is a schematic representation of an autosampler subsystem.

FIG. 3 is a schematic representation of an autosampler subsystem used in the MIPC system. This autosampler removes an aliquot having a predetermined volume from a selected well or vial (e.g., micro-centrifuge tube) supported in a multi-well 113. Microwell plates can have any predetermined number of wells 114 having a precise dimensional position for each well, such as the standard 96 well multi-well plate. The sampling needle 115 is supported on a sampling carriage 116. The sampling carriage 116 has a needle support 118 mounted for vertical movement on vertical support 117. Vertical support 117 is mounted for lateral movement on carriage 116. Lateral movement of the support 117 positions the needle above a selected well or the injector port 119 of injection valve 120. The flexible tubing 123 is mounted in sealed engagement with the needle 115 at one end and with the syringe needle 124 at the other end. The syringe needle 124 communicates with the inner volume of the syringe cylinder 125. The piston 126 is mounted on the syringe actuator rod 128 and forms a sealed engagement with the inner wall of the cylinder 125. In operation, vertical upward movement of the syringe actuator rod 128 displaces liquid in the cylinder 125, and vertical downward movement of the syringe actuator rod 128 pulls liquid into the syringe. Rod 128 is attached to clamp 130 which is supported for movement along guide element 132. When valve 122 is positioned to provide communication between the needle 124 and the tubing 123, the downward movement of the piston 126 pulls sample into the needle 115 from a well 114. When needle 115 is positioned above injector valve port 119, upward movement of the piston 126 discharges sample from needle 115 into port 119.

Conduit 131 extends from valve 122 to the cleaning solution reservoir 121. When valve 122 is in the position providing communication between the needle 124 and the conduit 131, the downward movement of the piston 126 draws cleaning solution into the needle. When the needle 115 is positioned above the injector port 119 and valve 122 is positioned to provide communication between the needle 124 and the conduit 123, upward movement of the piston 126 discharges cleaning solution into the injector port 119. Examples of suitable autosamplers include the HITACHI Model L-7250 Programmable Autosampler and the HTS PAL High Throughput Autosampler (Shimadzu, Columbia, Md.). The autosampler is preferably adapted for retaining the sample at a chilled temperature, e.g. 4–10° C.

Figure 4:
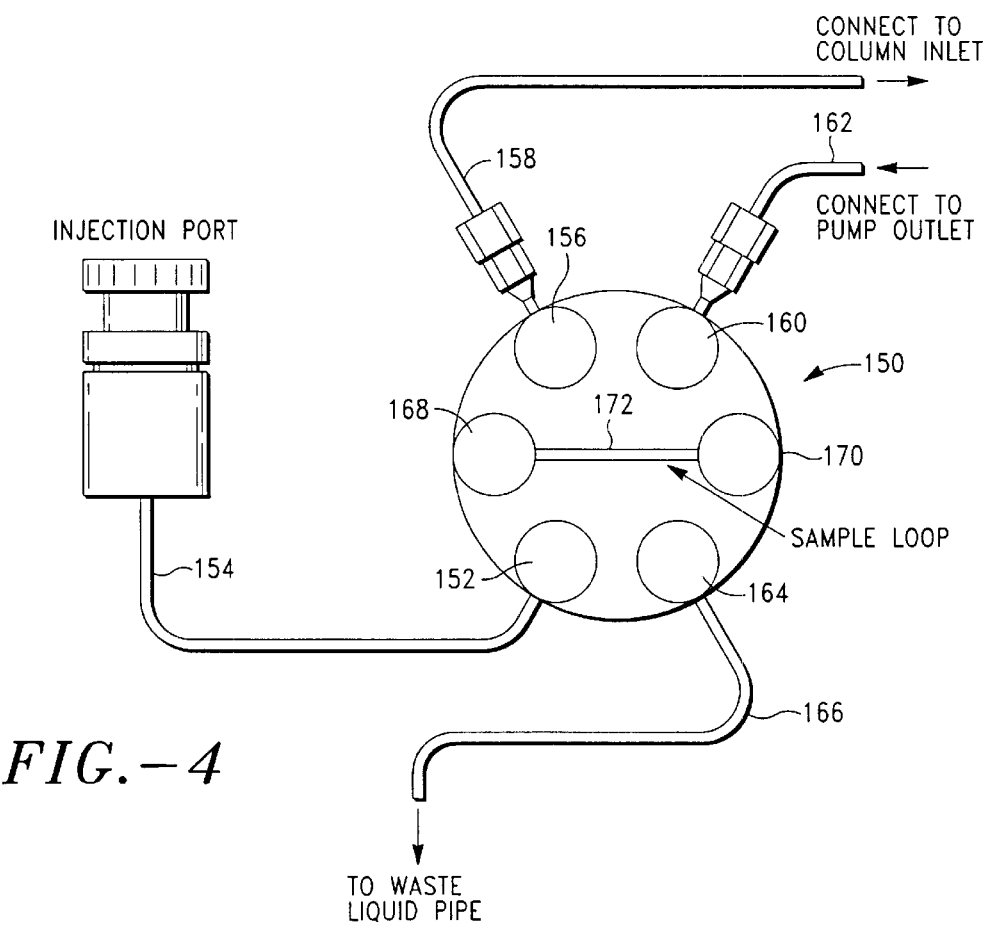
FIG. 4 is a schematic representation of an injection valve used in the MIPC system.

FIG. 4 is schematic representation showing the structure of the sample injection valve and cleaning solution injection valve for use in the MIPC system. The same valve structure can be used for both the sample injection and cleaning solution injection. The injection valve 150 is a six-port, rotary valve operated by a conventional valve motor such as a stepper motor (not shown). Exemplary valves include the LabPRO valves available from RHEODYNE (Cotati, Calif.). The valve has six external ports permanently connected to inlet and outlet conduits. External port 152 is connected with an injection line 154 for receiving a sample to be analyzed. External port 156 is connected with a column supply conduit 158 communicating with the separation column 78 (FIG. 1). External port 160 is connected with an inlet conduit 162 communicating with the outlet of pump 38 (FIG. 1). External port 164 is connected with a waste conduit 166. Opposed outlet ports 168 and 170 communicate with the opposed sample inlet and outlet ends of a sample loop 172. During the injection of cleaning solution, the valve injects a block of cleaning solution into the solvent stream, regenerating and cleaning the separation column and other components downstream of the injection, removing from the surfaces accumulated residues and any residual RNA remaining from prior segregation procedures.

The connections between the external ports and internal passages, and their operation in the cleaning solution injector valve 54 and sample injector valve 62 in FIG. 1 is described in FIGS. 5–8. The description hereinbelow is presented for the sample injection valve 62, but the same relationships and operation apply to the cleaning solution injection valve with the exception of the liquids being injected and their source.

Figure 5:
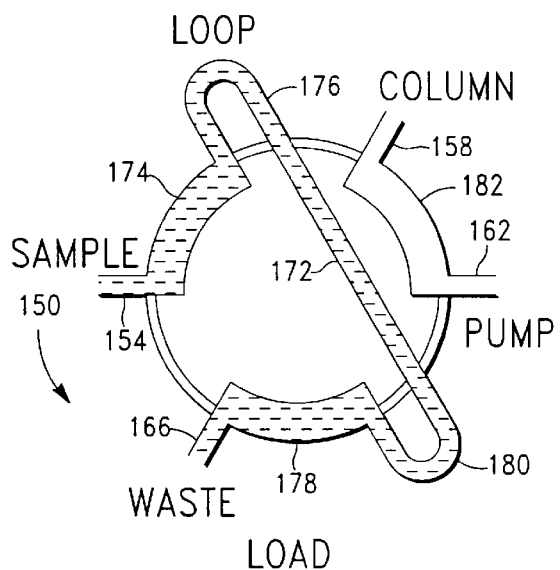
FIG. 5 is a schematic representation of an injection valve in the filled loop load position.
Figure 6:
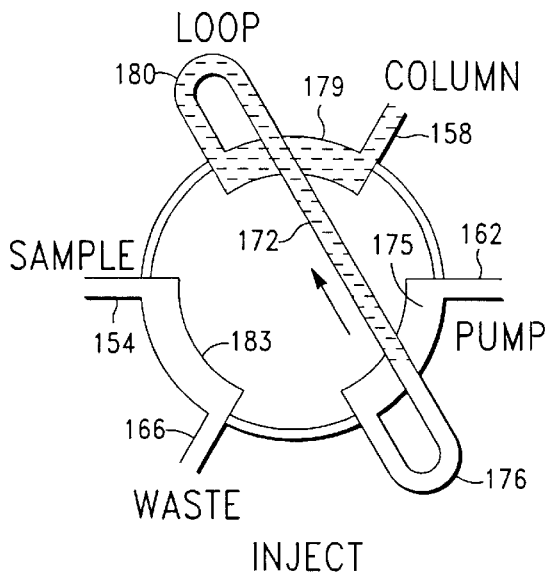
FIG. 6 is a schematic representation of an injection valve in the filled loop injection position.
Figure 7:
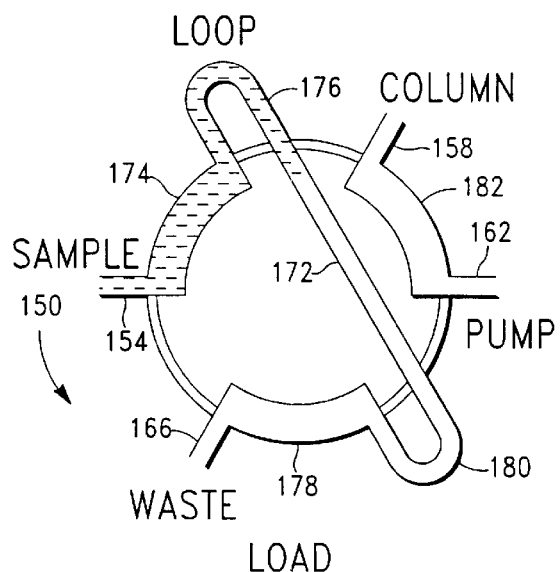
FIG. 7 is a schematic representation of an injection valve in the partial loop load position.
Figure 8:
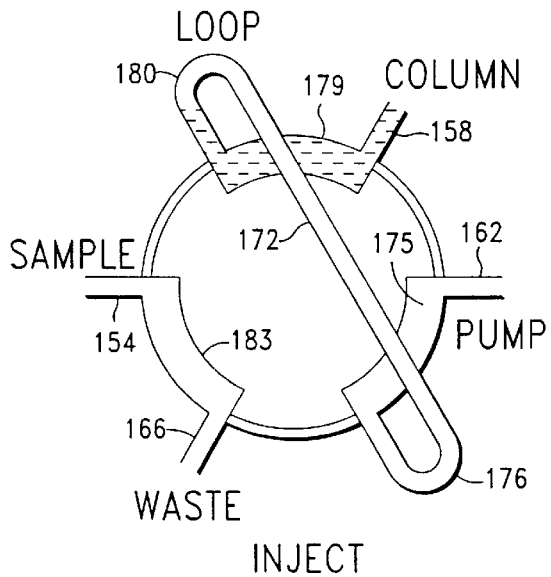
FIG. 8 is a schematic representation of the injection valve in the partial loop injection position.

FIGS. 5 and 6 describe the use of the valve for filled loop injection, the mode used when a larger volume of sample (or cleaning solution) is to be injected. FIG. 5 is a schematic representation of an injection valve in the sample load position, and FIG. 6 is a schematic representation of the injection valve in the injection position. In the load position shown in FIG. 5, a first internal passageway 174 of the valve connects the first end 176 of loop 172 with the sample injection line 154, and a second internal passageway 178 connects the second end 180 of loop 172 with the waste conduit 166. A third internal passageway 182 connects the pump outlet conduit 162 with the conduit 158 to the separation column 78. While sample from the injection port 154 is introduced into the sample loop 172 through passageway 174, any surplus or liquid in the loop 172 is expelled to the waste conduit 166 through passageway 178.

Simultaneously, mobile phase solutions flow from the pump conduit 162 to the separation column 78 through third conduit 182.

Rotation of the valve in the direction of arrow 150 to the injection position shown in FIG. 6 moves the internal passageways to establish a different set of connections with the inlet and outlet conduits. Passageway 179 connects one end 180 of the loop 172 with the conduit 158 leading to the separation column, and passageway 175 connects the other end 176 of the loop 172 with the inlet conduit 162 leading to the pump. Mobile phase solution from the pump enters passageway 175 and passes through the loop 172, expelling sample solution into the conduit 158 leading to the column and continues to rinse the loop, carrying any residue into the column conduit 158. Meanwhile, passageway 183 connects the sample injection conduit 154 to waste, permitting passage of cleaning solution, if desired, through passageway 183. This procedure provides a reliable injection of a measured volume of sample solution into the conduit leading to the separation column 78 (FIG. 1), the liquid passing through the prefilter 74 and temperature regulating coil 76 before it reaches the separation column.

The system of the invention incorporates oven temperature control means for controlling the temperature of the separation column and the mobile phase entering the column.

Figure 9:
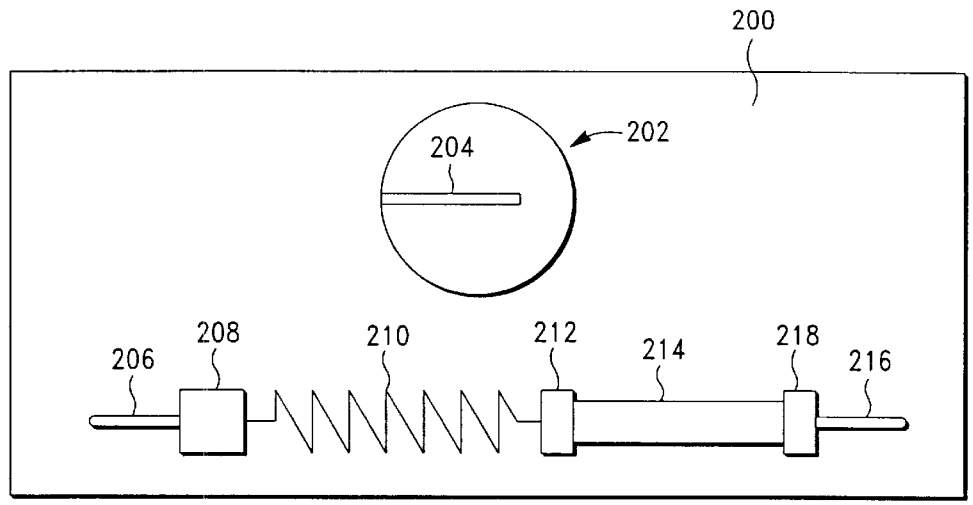
FIG. 9 is a front view of the separation compartment of an MIPC column oven.
Figure 10:
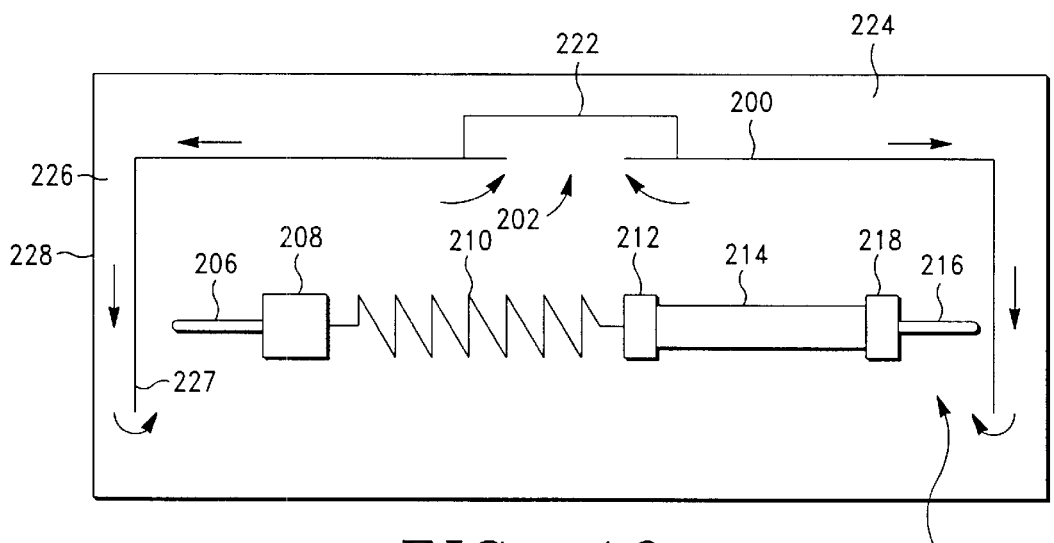
FIG. 10 is a top view of the HPLC DNA analyzer column oven shown in FIG. 9.

FIGS. 9 and 10 illustrate one embodiment of a temperature control means. FIG. 9 is a front view of the process compartment of an HPLC RNA analyzer column oven, and FIG. 10 is a top view of the HPLC RNA analyzer column oven shown in FIG. 9. The process compartment in the embodiment shown in FIGS. 9 and 10 is divided from the heating compartment by back wall 200 in which air exhaust port 202 is positioned. A metal bar 204 enclosing a temperature sensor such as a thermocouple or thermister is positioned in the port 202 to measure the temperature of the air passing through the port. Capillary tubing 206 leads from the sample injector (not shown) to a prefilter 208. Prefilter 208 is an inline filter or guard cartridge, such as described in U.S. Pat. No. 5,772,889, which removes contaminants from the incoming liquid. An elongated coil 210 of capillary tubing has an inlet end in communication with prefilter 208 for receiving mobile phase liquid therefrom. The elongated coil 210 has an outlet end communicating with the inlet end 212 of a separation column 214. Separation column 214 preferably contains MIPC separation media. Outlet tubing 216 leads from the outlet end 218 of the separation column 214 to detector 84 (FIG. 1). Coil 210 is a liquid heating coil made of a RNA compatible tubing such as titanium or PEEK. The length and diameter of tubing used is any length which is sufficient to enable liquid mobile phase passing therethrough to reach the equilibrium temperature of air in the processing compartment. A tubing length of from 6 to 400 cm and a tubing ID of from 0.15 to 0.4 mm is usually sufficient. Since the length of tubing 210 does not degrade the separation of components achieved by the system, the length can be selected based on the length required to achieve effective heating of the process liquids.

Referring to FIG. 10, air from the processing compartment 220 passes through the opening 202 in wall 200, through a heater/fan system 222 for temperature adjustment. The adjusted air received by the heating compartment 224 recycles back to the processing compartment 220 along the passageways 226 defined by the spacing between the sidewalls 227 and the outer oven wall 228. The heating coil in the embodiment shown in FIGS. 9 and 10 provides a temperature accuracy to within the range of ±0.2° C. and reduces the temperature equilibrium time between temperature settings to below 5 minutes for temperature changes of 5° C. and below 2 minutes for temperature changes of up to 1° C.

Figure 11:
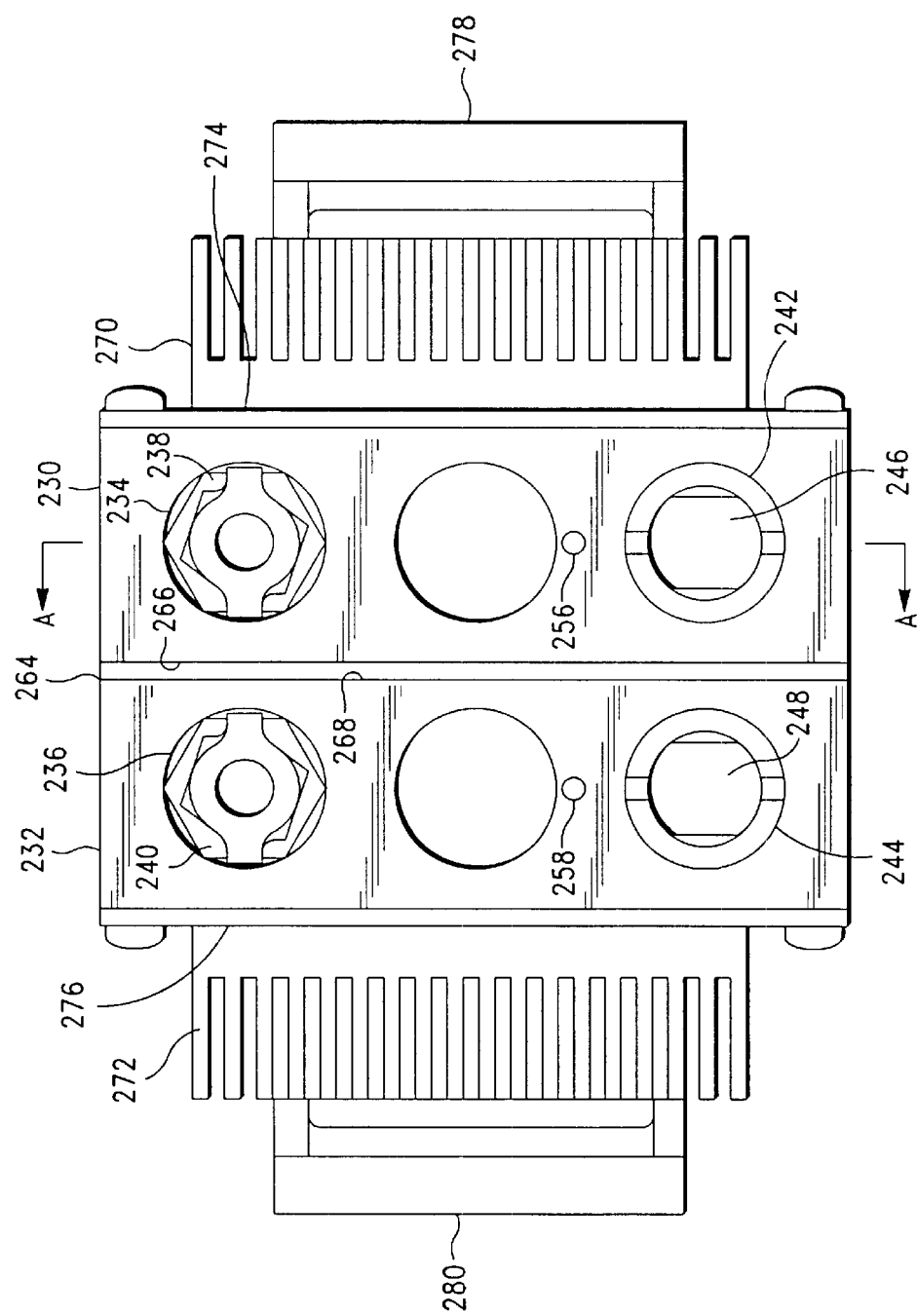
FIG. 11 is an end view of the compact column heater embodiment of this invention.
Figure 12:
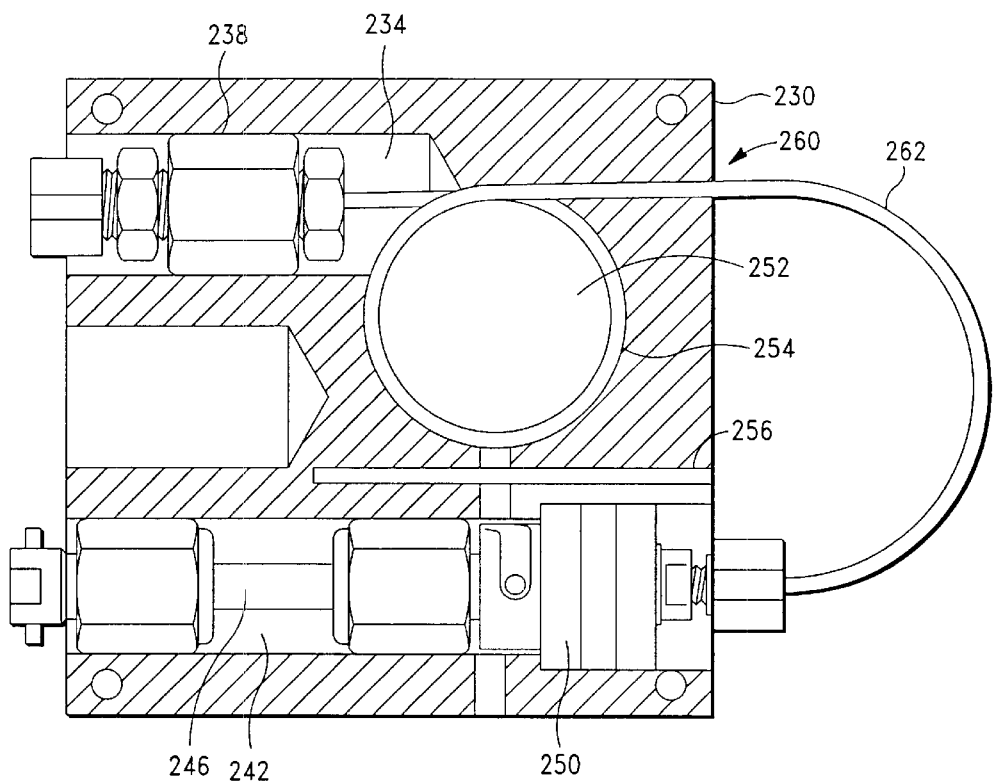
FIG. 12 is a cross-sectional view taken along the line A—A in FIG. 11.

FIGS. 11 and 12 illustrate another embodiment of a temperature control means. FIG. 11 is an end view of a compact column heater, and FIG. 12 is a cross-sectional view taken along the line A—A in FIG. 11. This embodiment relies on direct metal-to-metal conduction of heat to and from the system components and does not depend upon an air bath to achieve temperature changes and accuracy. This embodiment is shown for a two column system, although it could be used for a single column, if desired. It comprises heat conducting blocks (230,232) having receptacles sized and shaped to receive the system components. Filter cavity or prefilter receptacles (234,236) have inner surfaces which are sized to receive prefilters (238,240) and establish heat transfer contact with the outer surfaces thereof. Separation column receptacles (242,244) have inner surfaces sized to receive respective separation columns (246,248) and separation column couplers (250) (one is shown in FIG. 12) which connect capillary tubing to the respective separation columns. Receptacles (242,244) are sized and shaped to establish heat transfer contacts between the inner heat transfer surfaces of blocks (230,232) and the separation column components received therein. Capillary coil receptacles 252 (one is shown in FIG. 12) have an inner surface which is shaped to receive a coils of capillary tubing 254 (one is shown in FIG. 12) and to establish heat transfer contact with the outer surface thereof. In the embodiment shown in these figures, receptacles (234,236) and (242,244) can be cylindrical holes with approximately parallel central axes lying in a common plane. It would be readily apparent to a person skilled in the art that other configurations are equally suitable and all configurations are considered to be within the scope of this invention.

Temperature sensor receptacles (256,258) are provided in heat conducting blocks (230,232). Capillary receptacle passageways 260 for receiving connecting tubing 262 in a heat-conducting relationship are also provided in the heating-conducting block (230,232). The capillary coil receptacles 252 are shown in this figure to be cylindrical cavities with their axes perpendicular to the axes of receptacles (234,236) and (242,244). Optionally, a conductive metal cylinder (not shown) can be positioned within the capillary coils in heat conducting contact with the inner surfaces thereof to increase heat transfer area between the metal block heating assembly and the liquid in the coils. A KAPTON resistance heater or other type of heating unit 264 is positioned between and in heat-conducting contact with surfaces 266 and 268 of heating blocks (230,232) to transfer heat to the heat-conducting blocks. Heat sinks (270,272) are positioned in heat-conducting relationship with opposed cooling surfaces (274,276) of the heat conduct blocks (230, 232) to remove heat therefrom. Cooling fans 278 and 280 are in a heat removal relationship with the heat sinks 270 and 272 and are activated to accelerate heat removal therefrom.

The heat conducting blocks 230 and 232, and the heat sinks 270 and 272 are made of a material having high heat conductivity such as aluminum or copper, although they can be made of other heat-conducting solids such as ferrous metals or any other solid material having the requisite heat conductivity. Heat pipes can also be used as heat sinks.

The capillary tubing can be made of PEEK or titanium, although titanium is preferred for maximum heat transfer efficiency. With this improved heat transfer, the capillary coil can have a fully extended length as short as 5 cm although a minimum coil length of 10 cm is preferred. A longer coil of PEEK tubing would be required to achieve the same heat transfer as titanium capillary tubing.

The system shown in FIGS. 11 and 12 comprises two systems in mirror image. It will be readily apparent that for a single column, half the system would be sufficient and is intended to be included within the scope of this invention. The position, alignment and spacing of the receptacles are not a critical feature of this invention. Any alignment and configuration which provides a compact and heat-transfer efficient result is intended to be included within the scope of this invention.

The embodiments shown in FIGS. 11 and 12 provide a compact heater which is more responsive to heater controls, provides rapid changes from one temperature platform to another, and maintains a temperature accuracy within ±0.5° C. of a set temperature. The heat transfer rate obtained with the metal-to-metal contact between the heating block and the elements being heated is far greater than can be obtained in an air bath system, providing the more rapid response to a changed temperature and greater temperature accuracy. It also allows process liquid temperature adjustment with a shorter capillary tubing coil.

Figure 13:
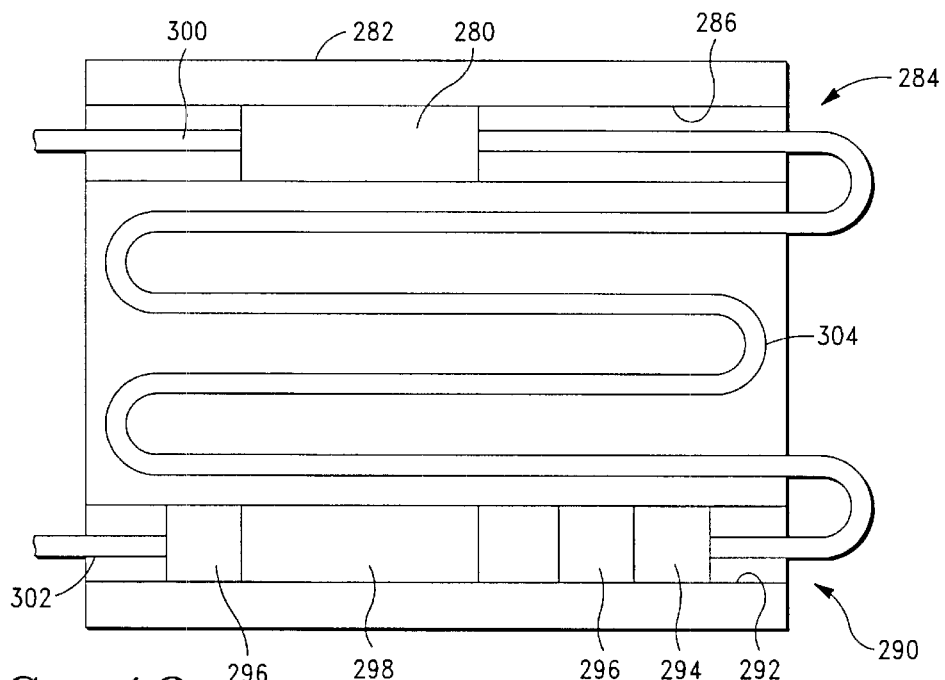
FIG. 13 is a schematic view of a Peltier heater/cooler embodiment of this invention.

In yet another illustration of a temperature control means, FIG. 13 shows a schematic view of a preferred Peltier heater/cooler embodiment. Heating block 282 is in conductive contact with a Peltier heating element (not shown) for heating or cooling required to reach and maintain a desired temperature. Channel 284 is a prefilter receptor having an inner surface 286 in heat conductive relationship with prefilter 288. Channel 290 is a column and column guard receptor having an inner surface 292 in heat conductive relationship with coupler 294 and end nut elements 296 of separation column 298. Capillary tubing 300 communicates with the prefilter 288 and the sample and solution sources (not shown). Capillary tubing 302 from the outlet of the separation column 288 communicates with an analyzer 84 (FIG. 1). Capillary tubing 304 connects the outlet end of the prefilter 288 with the coupler 294, which in turn communicates with the separation column 298. Capillary tubing 304 is received in a labyrinth-like configuration of channels in the heating block 282 to provide increased capillary length and surface contact between the capillary tubing 304 and the heating block 282. The configuration of the labyrinth and tubing can be any configuration which provides an adequate capillary length and surface contact, including additional loops and capillary placement of more than one pass per channel. The capillary tubing 304 can be PEEK or titanium, titanium being preferred because of its high heat conductivity. The heating block 282 can be any heat conductive metal. Aluminum or copper are preferred because of their higher heat conductivity, although ferrous metals such as steel can be used. The Peltier heater is controlled with a conventional temperature and control system (not shown) such as the systems used in Peltier thermocyclers. As with the embodiment shown in FIGS. 11 and 12, the temperature accuracy achieved by the Peltier heated block is ±0.5° C.

Features of improved air bath oven and solid block heating systems described hereinabove with respect to FIGS. 9–13 are described in greater detail in commonly owned, copending U.S. Pat. No. 6,103,112, the entire contents of which is hereby incorporated by reference.

Other examples of heating systems suitable for used in the subject invention include the L-7300 column oven (Hitachi) and the Column Heater available from BioRad (catalogue no. 125-0235).

In carrying out the MIPC method of the invention, the RNA sample to be analyzed is typically injected and premixed with the mobile phase prior to elution on the separation medium. The sample is then contacted directly with the separation media, or alternatively, is passed through a "pre-conditioning" tubing or pre-column to allow the sample and mobile phase to equilibrate before contact with the separation medium.

In one embodiment, the mobile phase components are introduced into a mixer inside the column oven and mixed prior to contact with the sample. Alternatively, the mobile phase components may be mixed at ambient temperature and contacted with the sample injector, also maintained at ambient temperature outside of the column oven. In a preferred embodiment, the sample is injected into the mobile phase, pre-equilibrated to the temperature of the column. In this manner, a near-direct connection between the column and the injector is provided to minimize diffusion and enhance sample resolution.

Alternately, when utilizing a low-pressure HPLC system, sample mixing typically occurs at ambient temperature. In instances in which the autosampler does not provide for heating the injection port to column temperature, standard HPLC tubing (e.g., 0.005–0.01" diameter) may be positioned between the injector and the column, to heat the mobile phase and induce denaturation of the polynucleotide sample. The tubing is preferably made of PEEK (polyether ether ketone) or titanium. The length of the tubing is typically determined based upon the efficiency of heat transfer. The entire length of the pre-column may be maintained at oven temperature, or, only a portion of the pre-column may be heated. The sample is passed through the pre-column and then contacted with the separation medium for subsequent elution.

Figure 14:
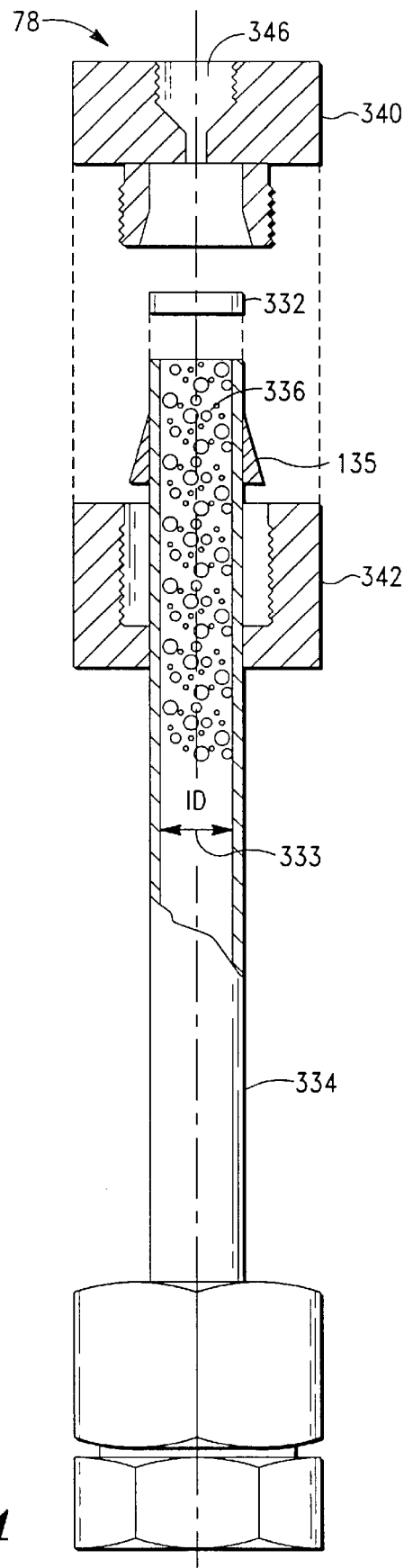
FIG. 14 is a representation of the physical structure of a representative reverse phase chromatographic column.

An important aspect of the present invention concerns the cross-sectional dimension of the separation column 78. FIG. 14 is a partially exploded representation of the physical structure of a representative separation column. The column comprises a cylinder or tube 334 with external ferrule 335 on both ends. The tube has internal diameter (ID) as shown at 333 and is filled with separation media 336. A porous frit 338 is held against the upper surface of the separation media by the end fitting 340. The end fitting 340 receives frit 338 and holds the frit against the end of the tube 334. The internally threaded nut 342 receives the externally threaded fitting 340 in a threaded engagement. The fitting 340 has an internally threaded end receptor 346 for receiving a capillary tubing end coupler (not shown).

The material comprising the cylinder 334 can be polymer or metal. Stainless steel tubes suitable for use in the present invention are available commercially, for example from Isolation Technologies Inc. (Hopedale, Mass.). Examples include stainless steel tubing having ID sizes such as 4.6, 6.5, 7.8, 10.0, 21.2, 30 and 50 mm. Columns as large as 500 mm to 1 m are also available and are suitable for use in the present invention. The column preferably includes porous frits 338 (e.g., as manufactured by Mott Corporation, Farmington, Conn.) inside the fittings on both ends and can include end seals that screw into the fittings (available from Upchurch Scientific, Oak Harbor, Wash. and/or Isolation Technologies).

The separation media 336 comprises organic polymer materials or inorganic materials having the requisite structure and non-polar surfaces. Suitable materials are described hereinbelow and in copending, commonly assigned U.S. patent application Ser. No. 09/183,123 (now U.S. Pat. No. 6,066,258) the contents of which are hereby incorporated by reference.

In one aspect, the present invention concerns a chromatographic method for segregating a mixture of RNA molecules having lengths exceeding about 100 nucleotides, the method comprising: a) applying a solution of said fragments and counterion reagent to a column containing polymeric beads having non-polar surfaces, wherein said beads have an average diameter of about 1 to about 100 microns; and b) eluting the RNA molecules with a mobile phase which includes counterion reagent and an organic component. In a preferred embodiment, the mixture is eluted from the separation medium at a minimum denaturing temperature.

In the practice of the method of the invention, a liquid sample containing RNA molecules is injected onto a MIPC chromatography column containing a reverse phase support. In MIPC, the RNA is paired with a counterion and then subjected to reverse phase chromatography using the non-porous beads as described herein. Aqueous mobile phase containing ion pairing reagent is applied to the column at an initial concentration of organic component that is low enough such that all of the RNA molecules of interest bind to the column. The RNA molecules elute as the concentration of organic component in the mobile phase is increased. The concentration of organic component preferably is applied as a gradient in order to elute the RNA molecules. The gradient can be a linear gradient, although curved or step gradients can also be used.

In a preferred embodiment of the method, the elution is carried out under conditions effective to denature the secondary structure of the RNA molecules. For example, the denaturation can be accomplished by conducting the elution at a temperature greater than about 60° C. and more preferably above 70° C. An operable temperature is within the range of about 40° C. to about 90° C.

In other embodiments, the denaturation can be accomplished by conducting the elution at a temperature of at least about 55° C., preferably above about 75° C., and more preferably above 80° C. The temperature is preferably within the range of about 75° C. to about 100° C. For some RNA segregations, the maximum temperature can be up to about 120° C.

The pH of the mobile phase is preferably within the range of about pH 5 to about pH 9, and optimally within the range of about pH 6 to about pH 7.5.

Fractions eluting from the MIPC system can be collected as a single fraction or as a plurality of fractions. The collection can be performed manually (e.g., from conduit 90) or using an automated fraction collector.

The method of the invention can be used to segregate molecules having lengths exceeding about 100 nt. The method is especially useful in segregating RNA molecules above a length exceeding about 200 nt. The method can also be used in segregating RNA molecules of about 50 to 200 nt from RNA molecules of about 500 to 2,000. The method can be used in segregating RNA molecules having lengths of about 500 to about 1,000 from molecules having lengths of about 3,000 to about 20,000. The method can be used in segregating RNA molecules having lengths within the range of about 200 nt to about 20,000 nt. The method can be used to segregate tRNA from rRNA, and can be used to segregate tRNA and rRNA from mRNA molecules which exceed the length of the largest rRNA.

MIPC segregation of RNA has the advantage of providing essentially pure and intact RNA molecules, or size ranges of RNA molecules, avoiding chemical covalent modification which can occur using prior art, gel-based, separation methods. Also, segregation by MIPC can be accomplished in about 10–30 min, in contrast to conventional gel chromatography which can require hours or days. The shorter processing times required in the present method decrease the chance for RNA degradation to occur.

Particular examples of the segregation of RNA molecules are described in the examples herein.

Figure 15:
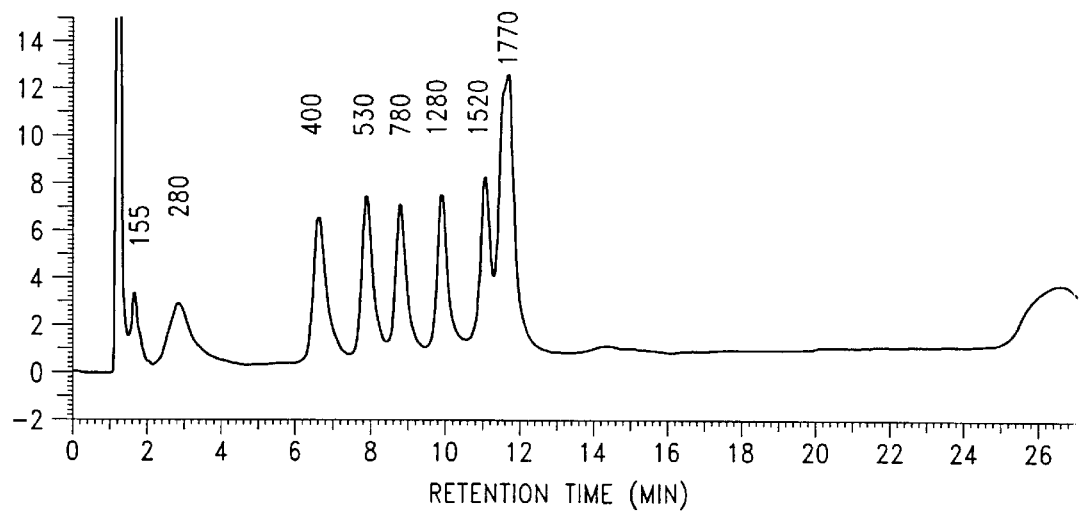
FIG. 15 is a chromatogram from a MIPC analysis of RNA size markers. Peaks are labeled with the number of nucleotides of the eluted molecules.
Figure 16:
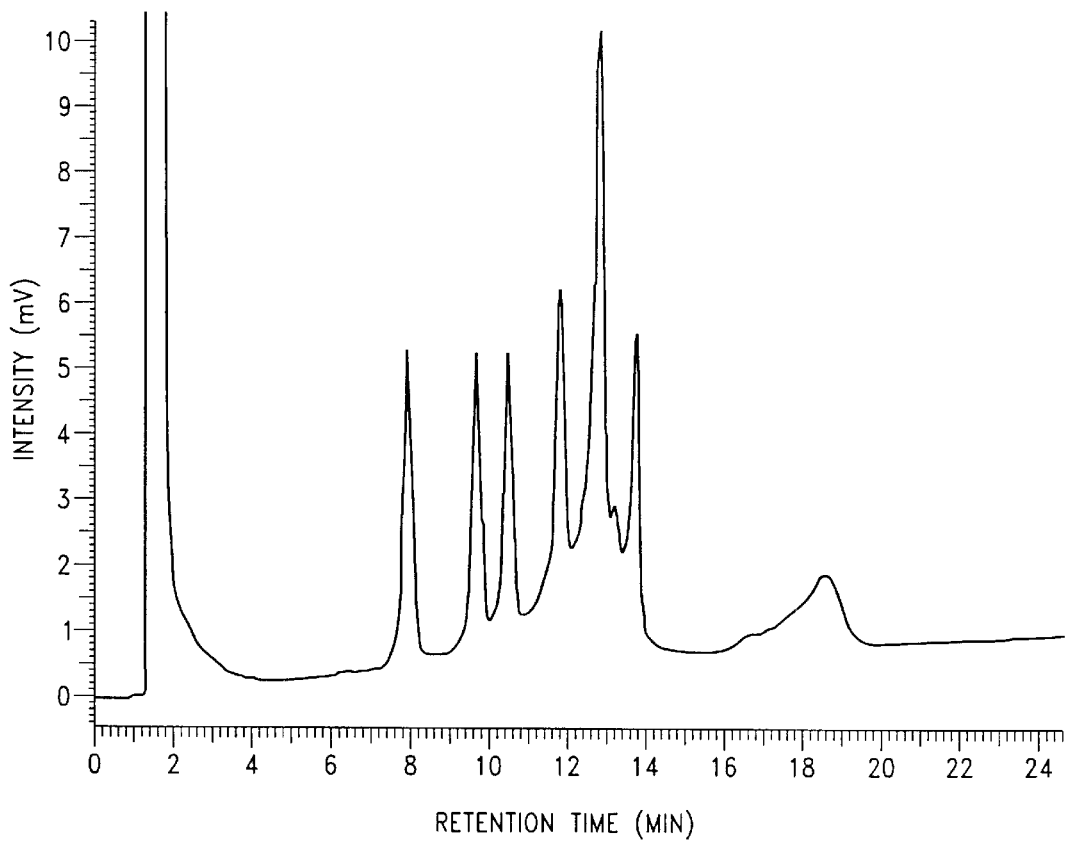
FIG. 16 is a chromatogram from a MIPC analysis of RNA size markers.

In the chromatogram shown in FIG. 15, as described in Example 1, RNA size standards ranging in size from 155 to 1770 nucleotides were segregated using the system and method of the present invention. FIG. 16 is another example of segregation of RNA size standards.

Another example of an RNA segregation is described in Example 2 (FIG. 17) in which a sample of total RNA from a plant source was applied to a reverse phase column of the invention and eluted at 75° C. Peaks were observed for different classes of RNA in order of their respective sizes with tRNA (70–150 nt) eluting first, followed by rRNA (1,500 to 3,700 nt). rRNA, the most abundant species, appeared as two large peaks between about 13–15 min. and had the greatest area under the curve. In order to enrich for mRNA, a portion of the plant total RNA was further purified using a spin column containing polystyrene-latex particles covalently linked to dT oligonucleotides, according to the instructions provided with the column (Catalog no. 70022, Qiagen). Analysis of the resulting product by MIPC (FIG. 18) indicated a decrease in rRNA (appearing at about 14 min) and a relative increase in an mRNA peak (appearing at about 17 min). A further decrease in the rRNA peak was observed after an additional spin column purification (FIG. 19).

Another representative example of an RNA segregation is described in Example 3 (FIG. 20). Fractions of mobile phase (0.9 mL each) were collected each minute from 5 to 13 minutes. Further work (data not shown) indicated that fractions 5–8 were each enriched for fragments under 2,000 nt. Fractions 9 and 10 were enriched for fragments between about 1,000 and about 15,000 nt. Fraction 11 was enriched for fragments having between about 2,000 and about 10,000 nt.

A further representative example of an RNA segregation is described in Example 4 (FIG. 21) in which a mixture of human brain mRNA was analyzed using a 50 mm×4.6 mm ID column. The mixture showed a single broad peak at about 9.9 min. Applicants surprisingly observed dramatic improvement in segregation of this mixture of when the elution was conducted using a column having an ID of 7.8 mm (FIG. 22) as described in Example 5. Additional peaks at about 9.9 min and 10.41 min were observed on the leading edge of the broad peak eluting at 11.8 min. Improved segregation of RNA molecules having lengths exceeding 100 nucleotides pairs is obtained using columns having internal diameters greater than about 5 mm. Improved resolution during the segregation of RNA by MIPC is obtained using a column having a ID of greater than 5 mm, preferably greater than about 7 mm, more preferably greater than about 10 mm. In other embodiments, improved segregation is obtained with a column can having an ID within the range of about 5 mm to about 1 m.

The present invention is based in part on Applicants' surprising discovery that segregation of RNA molecules by MIPC is improved when the segregation is conducted at temperatures greater than the minimal denaturing temperature. Temperature has a marked effect on the ability to analyze RNA molecules by MIPC. As shown in FIGS. 23–26, and as described in the Examples 12 and 13, temperature affected the MIPC analysis of RNA fragments. Both the resolution and the recovery improved when performing the segregation at elevated temperatures. For example, in comparing FIGS. 23–26, for the same injection quantity of RNA, peak width was reduced at higher temperature, and the peak height increased. Compared to the result obtained at 40° C., improved segregation was obtained when the temperature was 50° C. Further improvement was obtained at 65° C. Still further improvement was obtained at a temperature of 75° C. Thus, conducting the analysis at higher temperatures can result in improved resolution between components and allow more rapid RNA segregation. A non-limiting explanation for this observation is that running the segregation at the higher temperature eliminates the secondary structure from the RNA molecules which then exist in extended form. In the extended form, there are more sites to interact with the separation medium The present invention is also based in part on Applicants' surprising discovery that segregation of RNA molecules by MIPC is improved when the separation medium is free, or substantially free, from multivalent cations that are free to bind with the RNA molecules being segregated. Without wishing to be bound by theory, Applicants believe that when certain multivalent cations (e.g. Fe(III), Cr(II), or colloidal metal contaminants) are free to bind with the RNA molecules, then these multivalent cations interfere with the RNA segregation process. As described FIGS. 27–31, as described in the Examples hereinbelow, contamination of a separation column with multivalent cations, such as Cr(III), markedly inhibited the ability to analyze RNA molecules by MIPC. Subsequent treatment of the separation column with EDTA dramatically improved the analysis of RNA by MIPC.

In another aspect, the present invention provides a method for segregating a mixture comprising RNA molecules. In a preferred embodiment, the method includes (a) applying the mixture to a polymeric separation medium having non-polar surfaces, as described herein, and (b) segregating the mixture of RNA molecules. The method preferably includes eluting the mixture with a mobile phase containing a counterion agent and an organic solvent. In a preferred embodiment, the mixture is eluted from the separation medium at a temperature effective to fully denature all intramolecular hydrogen bonds between bases in the RNA molecules in the mixture. Also in a preferred embodiment, the surfaces are characterized by being substantially free from multivalent cations which are free to bind with the RNA molecules in the mixture. In a particular embodiment, the method comprises a) flowing the mixture through a separation column containing polymer beads having an average diameter of 0.5 to 100 microns, said beads being unsubstituted polymer beads or polymer beads substituted with a moiety selected from the group consisting of hydrocarbon having from 1 to 1,000,000 carbons, and b) segregating said mixture of RNA moleclues at a minimum denaturing temperature.

In a further aspect, the present invention provides a method for segregating a mixture comprising RNA molecules. In a preferred embodiment, the method includes (a) applying the mixture to a polymeric separation medium having non-polar surfaces, wherein the surfaces are characterized by being substantially free from multivalent cations which are free to bind with the RNA molecules in the mixture, and (b) segregating the mixture of RNA molecules. The method preferably includes eluting the mixture with a mobile phase containing a counterion agent and an organic solvent. In a preferred embodiment, the mixture is eluted from the separation medium at a minimum denaturing temperature.

In still another aspect, the invention involves a method in which a liquid sample containing RNA molecules is injected onto a MIPC chromatography column containing a reverse phase support. In the sample, the RNA molecules are paired with a counterion reagent and then subjected to reverse phase chromatography using the nonporous beads, or other media, as described herein. Aqueous mobile phase containing counterion reagent is applied to the column at an initial concentration of organic component that is low enough such that all of the RNA molecules of interest bind to the column. This process allows contaminants such as salts, buffers, proteins or other impurities to be removed from the bound RNA. The RNA molecules can be subsequently eluted as the concentration of organic component in the mobile phase is increased. The concentration of organic component preferably is applied as a gradient in order to elute the RNA molecules. The gradient can be a linear gradient, although curved or step gradients can also be used.

In a particular aspect, the invention involves a method for segregating RNA molecules from impurities. The method includes a) applying the RNA molecules to a Matched Ion Polynucleotide Chromatography column as described herein, and b) eluting the column to segregate the RNA molecules from the impurities. Example of such impurities include RNA degradation products, other polynucleotides, salts, buffers, and proteins. The elution is preferably conducted at a temperature that denatures the secondary structure of the RNA molecules. The method preferably includes detecting the presence of RNA molecules eluted from the column in the mobile phase, such as by UV detection. Mobile phase fractions containing the selected RNA molecules can be collected during the elution.

In another aspect, the invention involves a method for segregating a mixture comprising RNA molecules. The method includes a) applying the mixture to a polymeric separation medium having non-polar surfaces, wherein the surfaces are characterized by being substantially free from multivalent cations which are free to interfere with RNA segregation, and b) eluting the RNA molecules with a mobile phase which includes counterion reagent and an organic component. Examples of such multivalent metal cations include Fe(III), Cu(II), Cr(III), and colloidal metal contaminants. Step (b) preferably includes, with a mobile phase containing a counterion agent, eluting the mixture at a minimum denaturing temperature. For example, the eluting can be carried out at a temperature greater than about 55° C. The eluting can be carried out at a temperature within the range of about 60° C. to about 90° C. The separation medium can include polymeric beads having non-polar surfaces, wherein the beads have an average diameter of about 1 to about 100 microns. Alternatively, the non-polar surfaces can be the surfaces of interstitial spaces of a polymeric monolith. The surfaces of the monolith can be unsubstituted or substituted with a hydrocarbon group having from 1 to 1,000,000 carbons.

In general, the preferred reverse phase beads for use in the present invention is that they must have a surface that is either intrinsically non-polar or be bonded with a material that forms a surface having sufficient non-polarity to interact with a counterion agent.

The non-porous polymeric beads can have an average diameter of about 0.5–100 microns; preferably, 1–10 microns; more preferably, 1–5 microns. Beads having an average diameter of 1.0–3.0 microns are most preferred.

Without wishing to be bound by theory, Applicants believe that the beads which are operable in RNA segregation as described herein have a pore size which essentially excludes the RNA molecules being separated from entering the bead. As used herein, the term "nonporous" is defined to denote a bead which has surface pores having a diameter that is less than the size and shape of the smallest RNA molecule in the mixture in the solvent medium used therein. Included in this definition are polymer beads having these specified maximum size restrictions in their natural state or which have been treated to reduce their pore size to meet the maximum effective pore size required.

The surface conformations of nonporous beads of the present invention can include depressions and shallow pit-like structures which do not interfere with the segregation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the RNA into the interconnected pore structure and into the bead impair the segregation of RNA molecules or result in segregations that have very long retention times. In MIPC, however, the preferred beads are "nonporous" and the polynucleotides do not enter the bead structure.

Chromatographic efficiency of the column beads is predominantly influenced by the properties of surface and near-surface areas. For this reason, the following descriptions are related specifically to the close-to-the-surface region of the polymeric beads. The main body and/or the center of such beads can exhibit entirely different chemistries and sets of physical properties from those observed at or near the surface of the polymeric beads of the present invention.

The nonporous polymeric beads of the present invention can be prepared by a two-step process in which small seed beads are initially produced by emulsion polymerization of suitable polymerizable monomers. The emulsion polymerization procedure of the invention is a modification of the procedure of Goodwin, et al. (Colloid & Polymer Sci., 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term "alkyl" as used herein in reference to the beads of the present invention is defined to include alkyl and alkyl substituted aryl groups, having from 1 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

In the present invention, successful segregation of RNA molecules can be achieved using underivatized nonporous beads as well as using beads derivatized with alkyl groups having 1 to 1,000,000 carbons. In preferred embodiments, the polymer is unsubstituted or is substituted with a moiety selected from the group consisting of methyl, ethyl, or hydrocarbon having from 23 to 1,000,000 carbons.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly(ethylvinylbenzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, preferably provides a nonporous, non-reactive, and non-polar surface for the MIPC segregation.

In another embodiment of the present invention, the separation medium can be in the form of a polymeric monolith such as a rod-like monolithic column. The monolithic column is polymerized or formed as a single unit inside of a tube. The through-pore or interstitial spaces provide for the passage of eluting solvent and analyte materials. The segregation is performed on the stationary surface. The surface can be porous, but is preferably nonporous. The form and function of the segregations are identical to columns packed with beads. As with beads, the pores contained in the rod must be compatible with RNA molecules and not trap the material. The rod preferably is characterized by being substantially free from multivalent cations which are free to bind with RNA.

The molded polymeric rod of the present invention can be prepared by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(glycidyl methacrylate-co-ethylene dimethacrylate), poly(styrene-divinylbenzene) and poly(ethylvinylbenzene-divinylbenzene. The rod can be unsubsituted or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like. In a preferred embodiment, the alkyl group has 1–24 carbons. In a more preferred embodiment, the alkyl group has 1–8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al. (*J. Chromatog. A* 699:230 (1994)), Petro et al. (*Anal. Chem.* 68:315 (1996)), and the following U.S. Pat. Nos. 5,334,310; 5,453,185; 5,522,994 (to Frechet).

In an important aspect of the present invention, the beads and other media of the invention are characterized by being substantially free from multivalent cations which are free to bind with RNA. The preferred beads are characterized by having been subjected to precautions during production, including a decontamination treatment, such as an acid wash treatment or treatment with a multivalent cation binding agent, designed to substantially eliminate any multivalent cation contaminants which can interfere with the segregation of RNA molecules (e.g. Fe(III), Cr(III), or colloidal metal contaminants). Preferably, only very pure, non-metal containing materials are used in the production of the beads in order that the resulting beads will have minimum metal content.

In addition to the beads themselves being substantially metal-free, Applicants have also found that, to achieve optimum peak segregation during MIPC, the separation column and all process solutions held within the column or flowing through the column are preferably substantially free of multivalent cation contaminants which are free to bind with RNA. As described in commonly owned U.S. Pat. Nos. 5,772,889; 5,997,742; and 6,017,457 this can be achieved by supplying and feeding solutions that enter separation column with components which have process solution-contacting surfaces made of material which does not release multivalent cations into the process solutions held within or flowing through the column, in order to protect the column from contamination with multivalent cations that can interfere with the segregation of RNA molecules. The process solution-contacting surfaces of the system components are preferably material selected from the group consisting of titanium, coated stainless steel, passivated stainless steel, and organic polymer.

There are two places where multivalent cation binding agents, e.g., chelators, can be used in RNA segregation using MIPC. In one embodiment, these binding agents can be incorporated into a solid through which the mobile phase passes. Contaminants are trapped before they reach places within the system that can harm the segregation process. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In an embodiment of the instant invention, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent preferably does not interfere with the chromatographic process. The concentration of the binding agent in the mobile phase is typically in the range of 0.1 to 10 mM, and often 1 mM.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α', α''-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation binding agent is EDTA.

To achieve optimal results, it is generally necessary to tightly pack the chromatographic column with the solid phase polymer beads. Any known method of packing the column with a column packing material can be used in the present invention to obtain adequate high resolution segregation of RNA molecules. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a 50×7.8 mm ID column, 3.0 grams of beads can be suspended in 15 mL of methanol with the aid of sonication. The suspension is then packed into the column using 100 mL of methanol at 8,000 psi pressure. This improves the density of the packed bed.

There are several types of counterions suitable for use with MIPC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

The purpose of the alkyl group is to impart a nonpolar character to the RNA through a matched ion process so that the RNA can interact with the nonpolar surface of the reverse phase media. The requirements for the extent of nonpolarity of the counterion-RNA pair depends on the polarity of the reverse phase media, the solvent conditions required for RNA segregation, the particular size and type of molecules being segregated. For example, if the polarity of the reverse phase media is increased, then the polarity of the counterion agent may have to change to match the polarity of the surface and increase interaction of the counterion-RNA pair. Triethylammonium acetate is preferred although quaternary ammonium reagents such as tetrapropyl or tetrabutyl ammonium salts can be used when extra nonpolar character is needed or desired.

In the mobile phase of the present method, an organic component that is water soluble is preferably used, for example, alcohols, nitriles, dimethylformamide (DMF), tetrahydrofuran (THF), esters, and ethers. Water soluble solvents are defined as those which exist as a single phase with aqueous systems under all conditions of operation of the present invention. Organic components which are particularly preferred for use in the method of this invention include solvents such as methanol, ethanol, 2-propanol, 1-propanol, tetrahydrofuran (THF), and acetonitrile, with acetonitrile being most preferred overall.

In some cases, it may be desired to increase the range of concentration of organic solvent used to perform the segregation. For example, increasing the alkyl length on the counterion agent will increase the nonpolarity of the counterion-RNA pair resulting in the need to either increase the concentration of the mobile phase organic component, or increase the strength of the organic component type. There is a positive correlation between concentration of the organic component required to elute a fragment from the column and the length of the fragment. However, at high organic component concentrations, the RNA could precipitate. To avoid precipitation, a strong organic component or a smaller counterion alkyl group can be used. The alkyl group on the counterion reagent can also be substituted with halides, nitro groups, or the like to moderate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkylmmonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography, 2nd Ed.*, Dr. Alfred H üthig Verlag Heidelberg (1987). Counterion agents that are volatile are preferred for use in the method of the invention, with triethylammonium acetate (TEAA) and triethylammonium hexafluoroisoropyl alcohol being most preferred.

Other features of the invention will become apparent in the course of the following descriptions of exemplary embodiments which are given for illustration of the invention and are not intended to be thereof.

EXAMPLE 1

RNA Segregation of an RNA Sizing Standard by MIPC using a 7.8 mm ID Column

MIPC analysis of a 0.16–1.77 kb RNA ladder (Catalog no. 15623010, Life Technologies) was performed using octadecyl modified, nonporous poly(styrene-divinylbenzene) beads packed in a 50 mm×7.8 mm ID reverse phase column (DNASEP® cartridge, Transgenomic, Inc., San Jose, Calif.) and using a WAVE® Nucleic Acid Fragment Analysis System (Transgenomic). This system included a L-7420 UV-Vis detector, a Model L-7100 pump, and a Model L-7250 autosampler (Hitachi) and a Degassit Model 6324 degasser. Buffer A: 0.1 M TEAA, pH 7.0; buffer B: 0.1 TEAA, 25% (v/v) acetonitrile, pH 7.0. The buffer stock solutions were obtained form Transgenomic. The gradient conditions were as follows:

| Time (min) | % B |
| --- | --- |
| 0.0 | 38 |
| 1.0 | 40 |
| 16 | 60 |
| 22 | 66 |
| 22.5 | 70 |
| 23 | 100 |
| 24 | 100 |
| 25 | 38 |
| 27 | 38 |

The flow rate 0.9 mL/min and the column temperature was 75.0° C. UV detection was performed at 260 nm. The injection volume was 5.0 µL. The sample contained a mixture of eight RNAs having the nucleotide lengths as shown in FIG. 15.

Prior to the injection, the column was equilibrated with 75% acetonitrile for 30–45 min at a flow rate of 0.9 mL/min. The column was then equilibrated using 38% B for 30 min. Prior to the elution of RNA, two control gradient elutions (using the same gradient conditions as for the RNA) were performed: a first injection of 10 µL of 0.5 mM EDTA and a second injection of 10 µL of nuclease free water (Catalog no. 9930, Ambion, Inc., Austin, Tex.). These two injections (data not shown) demonstrated that the column was free from contamination.

Another sizing standard (catalog no. 1062611, Roche Molecular Biochemicals, Indianapolis, Ind.) was similarly analyzed as shown in FIG. 16. 1 µg RNA was injected in a volume of 1 µL.

In preparing the mRNA sample for injection, all chemicals were of the highest purity grade available for molecular biology. Solutions, glassware, and small instruments were sterilized whenever possible. Liquid transfers were made using RNase free pipette tips (Rainin Instrument Co., Inc., Woburn, Mass.). All manipulations were performed wearing surgical gloves.

EXAMPLE 2

RNA Segregation of Tobacco Plant RNA by MIPC using a 7.8 mm ID Column

Total RNA was extracted from the flower of tobacco plant (*Nicotiana tabacum* cv. Wisconsin 38) by an acid guanidinium thiocyanate phenol-chloroform extraction method, and precipitated with 4 M lithium chloride (Chomczynski, et al., Anal. Biochem. 162:156–159 (1987) as described in Bahrami, et al., Plant Molecular Biology, 39:325–333 (1999).

Figure 17:
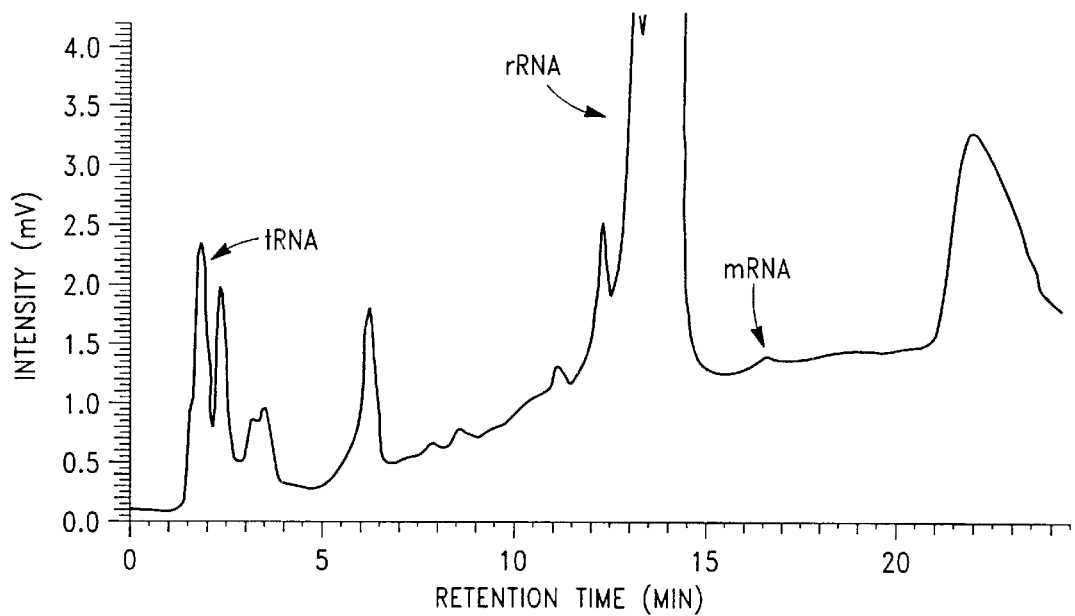
FIG. 17 is a chromatogram from a MIPC analysis of total RNA from a plant extract.
Figure 18:
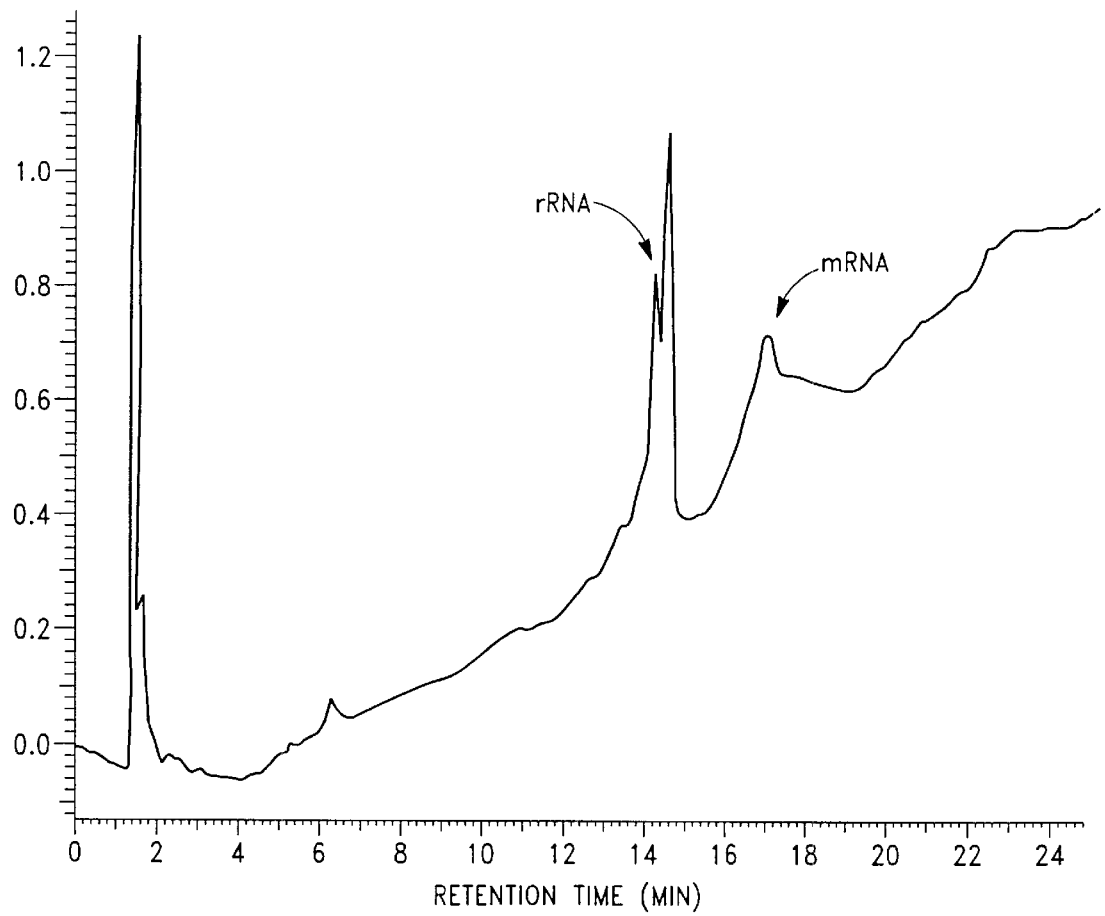
FIG. 18 is a chromatogram from a MIPC analysis of RNA from a plant extract after a first affinity purification.

MIPC analysis of total RNA from the plant extract was performed using octadecyl modified, nonporous poly (styrene-divinylbenzene) beads packed in a 50 mm×7.8 mm ID reverse phase column (DNASEP® cartridge, Transgenomic) and using a WAVE® Nucleic Acid Fragment Analysis System (Transgenomic). Buffer A: 0.1 M TEAA, pH 7.0; buffer B: 0.1 TEM, 25% (v/v) acetonitrile, pH 7.0. The gradient conditions were as described in Example 1. The volume injected was 2 µL (containing 1.54 µg RNA). The chromatogram is shown in FIG. 17.

mRNA was extracted from 50 µg of the total RNA preparation using the OLIGOTEX mRNA Purification System from Qiagen and following the procedures supplied with the kit (catalog no. 70022). A portion of the extracted mRNA was analyzed by MIPC (FIG. 18) using the elution conditions described in Example 1. The product of the first OLIGOTEX extraction was re-extracted, and a portion of the product was again analyzed by MIPC (FIG. 19).

EXAMPLE 3

RNA Segregation of Mouse Brain mRNA by MIPC using a 7.8 mm ID Column

5 µL (4.5 µg RNA) of mouse brain mRNA was subjected to MIPC analysis, using elution conditions as described in Example 1, with the resulting chromatograph shown in FIG. 20.

EXAMPLE 4

RNA Segregation of Human Brain mRNA by MIPC using a 4.6 mm ID Column

MIPC analysis of human brain mRNA (Catalog no. 6516-1, Clontech Laboratories, Inc., Palo Alto, Calif.) was performed using octadecyl modified, nonporous poly(styrene-divinylbenzene) beads packed in a 50 mm×4.6 mm ID reverse phase column (DNASEP® cartridge, Transgenomic) and using a WAVE® Nucleic Acid Fragment Analysis System (Transgenomic). Buffer A: 0.1 M TEAA, pH 7.0; buffer B: 0.1 TEAA, 25% (v/v) acetonitrile, pH 7.0. The gradient conditions were as follows:

| Time (min) | % B |
| --- | --- |
| 0.0 | 38 |
| 1.0 | 40 |
| 16 | 60 |
| 22 | 66 |
| 22.5 | 70 |

Figure 21:
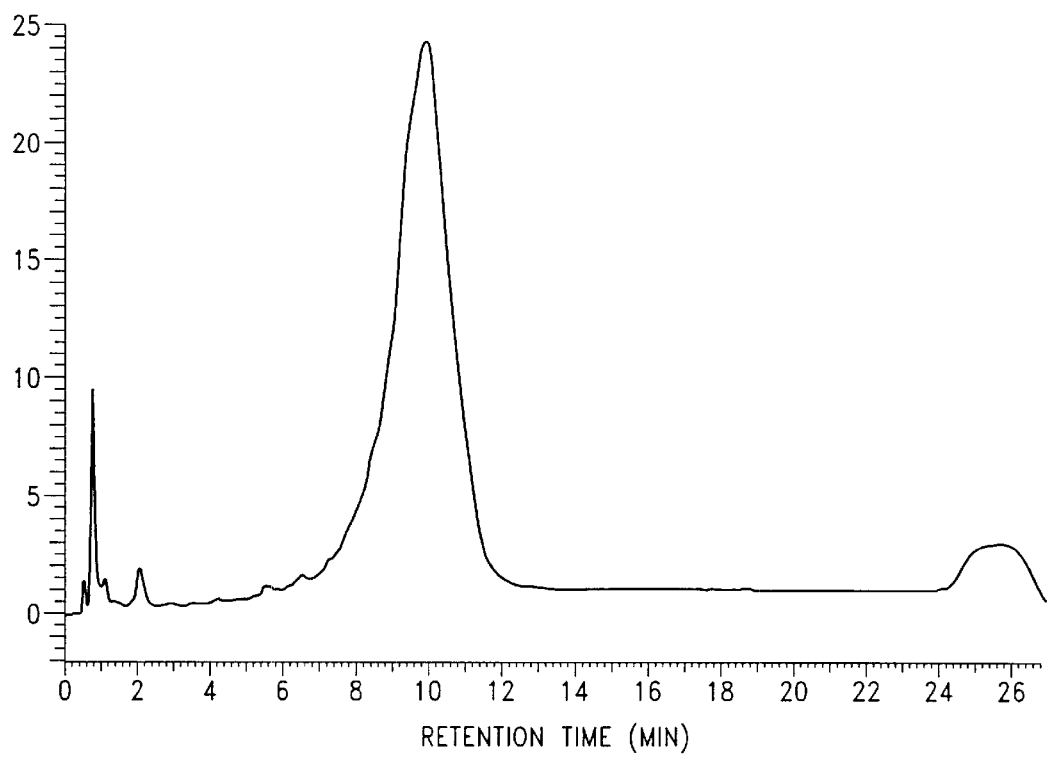
FIG. 21 is a chromatogram from a MIPC analysis of human brain mRNA.

The flow rate was 0.9 mL/min and the column temperature was 75.0° C. UV detection was performed at 260 nm. Injection volume was 4.5 µL. The chromatogram is shown in FIG. 21.

EXAMPLE 5

RNA Segregation of Human Brain mRNA by MIPC using a 7.8 mm ID Column

Figure 22:
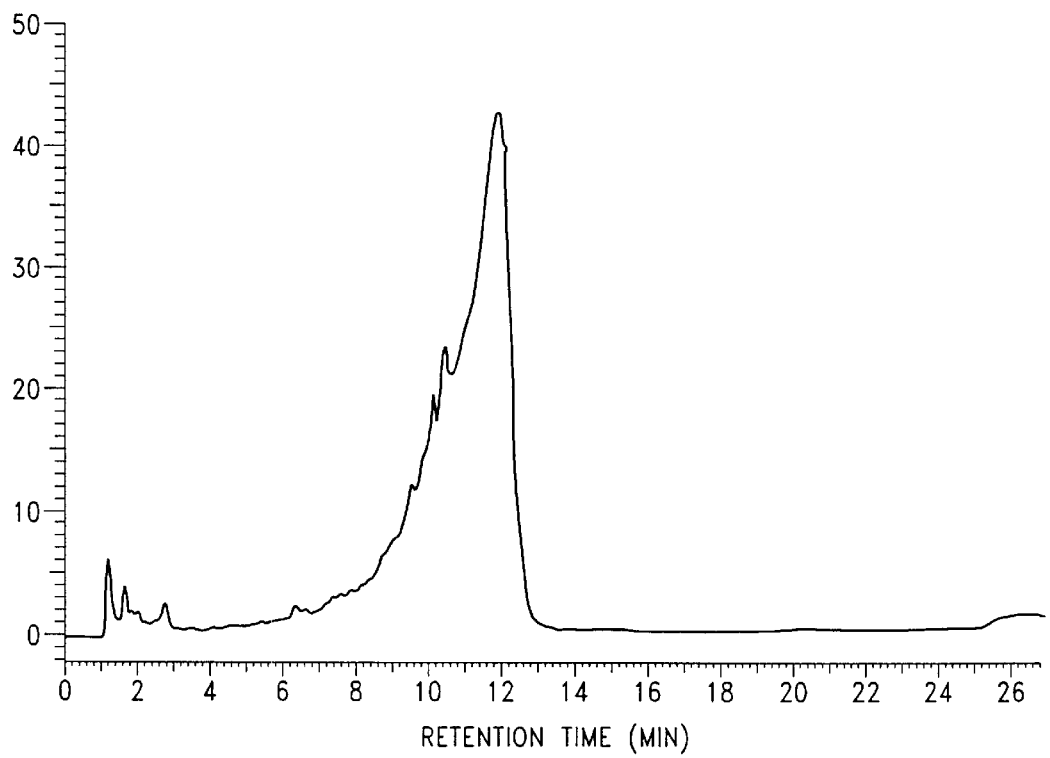
FIG. 22 is a chromatogram from a MIPC analysis of human brain mRNA.
Figure 25:
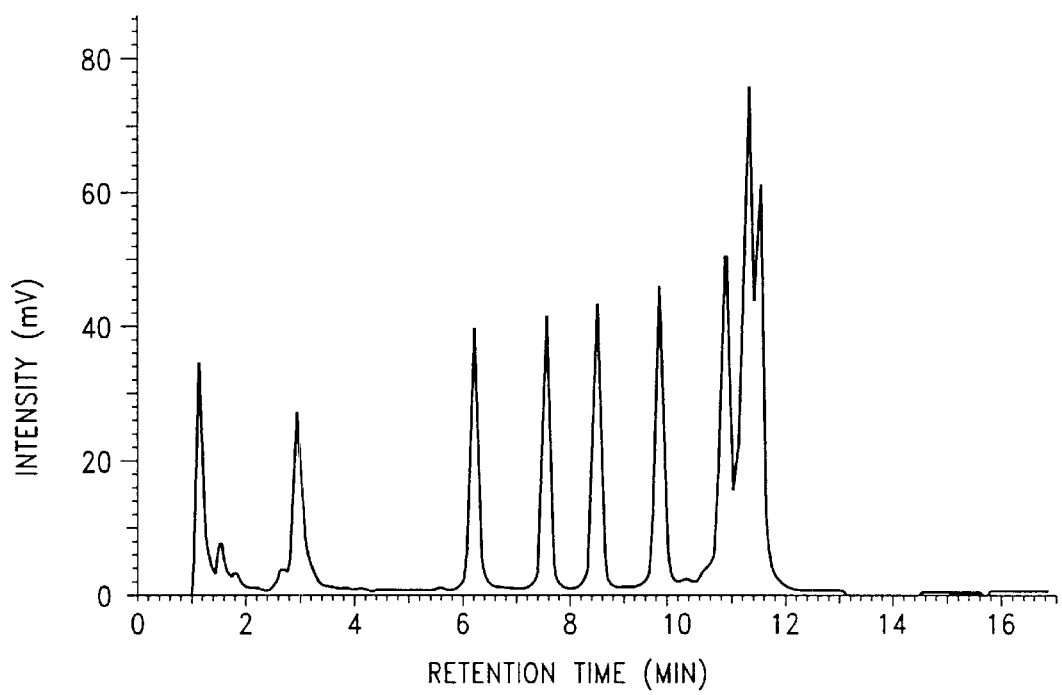
FIG. 25 illustrates an elution profile from MIPC analysis of RNA size markers carried out at a column temperature of 65° C.

MIPC analysis was performed using the same mRNA sample and conditions as described in Example 4 except that the column was replaced by a 50 mm×7.8 mm ID column. The injection volume was 5.5 µL. The chromatogram is shown in FIG. 22.

EXAMPLE 6

Preparation of nonporous poly(styrene-divinylbenzene) particles

Sodium chloride (0.236 g) was added to 354 mL of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 mL of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 mL volume of suspension resulting from the first step. The amount of polymerized styrene in 1000 mL was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased.

The protocol for the second step is based on the activated swelling method described by Ugelstad et al. (*Adv. Colloid Interface Sci.*, 13:101–140 (1980)). In order to initiate activated swelling, or the second synthetic step, the aqueous suspension of polystyrene seeds (200 ml) from the first step was mixed first with 60 mL of acetone and then with 60 mL of a 1-chlorododecane emulsion. To prepare the emulsion, 0.206 g of sodium dodecylsulfate, 49.5 mL of deionized water, and 10.5 mL of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C.

Following the removal of acetone, the swollen beads were further grown by the addition of 310 g of a ethyldivinylbenzene (DVB) (1:1.71) mixture also containing 2.5 g of dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30 Å).

After drying, the dried beads (10 g) from step two were washed four times with 100 mL of n-heptane, and then two times with each of the following: 100 mL of diethylether, 100 mL of dioxane, and 100 mL of methanol. Finally, the beads were dried.

EXAMPLE 7

Alkylation of Poly(Styrene-Divinylbenzene) Polymer Beads

The following procedures were carried out under nitrogen (Air Products, Ultra Pure grade, Allentown, Pa.) at a flow rate of 250–300 mL/min. 25 g of the beads prepared in Example 5 were suspended in 150–160 g of 1-chlorooctadecane (product no. 0235, TCI America, Portland, Oreg.) using a bow shaped mixer (use a 250 mL wide neck Erlenmeyer flask). The temperature was set to 50–60° C. to prevent the 1-chlorooctadecane from solidifying. Larger pieces of polymer were broken up to facilitate suspending. The solution was mixed using a stirrer (Model RZRI, Caframo, ONT NOH2T0, Canada) with the speed set at 2. The polymer suspension was transferred into a three neck bottle (with reflux condenser, overhead stirrer and gas inlet). 52–62 g of 1-chlorooctadecane were used to rinse the Erlenmeyer flask and were added to the three neck bottle. The bottle was heated in an ethylene glycol bath set at 80° C. The solution was mixed using a stirrer (Caframo) with the speed set at 0. After 20 minutes, the reaction was started by addition of 1.1 g $AlCl_3$ powder (product no. 06218, Fluka, Milwaukee, Wis.) and continued for 16–18 h.

After the reaction, the polymer was separated from excess 1-chlorooctadecane by centrifugation followed by consecutive washing steps:

| Addition | Comment |
| --- | --- |
| 50 mL conc. HCl, 50–60 mL n-heptane | 4 repetitions, with recycled heptane |
| 100 mL $H_2O$, 50–60 mL n-heptane | 1 repetition, with fresh heptane |
| 50 mL conc. HCl, 50–60 mL n-heptane | 1 repetition, with fresh heptane |
| 100 mL $H_2O$, 50–60 mL n-heptane | 1 repetition, fresh heptane |
| 150 mL $H_2O$, no n-heptane | 3 repetitions, use plastic stirrer to break up chuncks of polymer beads. Repeat steps 4 and 5 three times. Shake for two minutes with no centrifugation. |
| 100 mL THF | 3 repetitions |
| 100 mL THF/n-heptane | 1 repetition |
| 100 mL n-heptane | 1 repetition |
| 100 mL THF | 1 repetition |
| 100 mL $CH_3OH$ | 4 repetitions |

In the steps where aqueous solvents (HCl or $H_2O$) were used, the polymer was shaken for 30 seconds with the aqueous phase before adding n-heptane. n-Heptane was then added and the mixture was shaken vigorously for 2 min. After the final polymeric beads were dried at 40–50° C. for 2–3 hr, they were ready for packing.

EXAMPLE 8

Acid Wash Treatment

The beads prepared in Example 7 were washed three times with tetrahydrofuran and two times with methanol.

Finally the beads were stirred in a mixture containing 100 mL tetrahydrofuran and 100 mL concentrated hydrochloric acid for 12 hours. After this acid treatment, the polymer beads were washed with a tetrahydrofuran/water mixture until neutral (pH=7). The beads were then dried at 40° C. for 12 hours.

EXAMPLE 9

Column Packing Procedure

After weighing out 3 grams of oven dried polymeric beads from Example 8, a slurry was formed with 10 mL tetrahydrofuran (THF) and place in a sonicator under a fume hood for 15 min. 5 mL of THF and 5 mL of methanol (MeOH) were added followed by sonication for an additional 10 min. A packing assembly was pre-filled with 20 mL MeOH. The slurry was slowly poured into the packing assembly. A Haskel pump (Haskel International, Inc., Burbank, Calif.) was turned on and the packing pressure was slowly increased to 5000 psi for the initial packing phase. After 10 min, the packing pressure was slowly increased to 9000 psi and the secondary packing phase set for 20 min. After 20 min, the packing eluent was changed from MeOH to 0.05 M $Na_4EDTA$. The final packing phase was set for 40 min.

EXAMPLE 10

Preparation of a Non-Polar Organic Polymer Monolith Chromatography Column

A chromatography tube in which the monolith polymeric separation medium is prepared is made of stainless steel. The monomers, styrene (Sigma-Aldrich Chemical Corp.) and divinylbenzene (Dow Chemical Corp.) are dried over magnesium sulfate and distilled under vacuum.

To a solution of a 1:1 mixture by volume of the distilled styrene and divinylbenzene, containing 1% by weight (with respect to monomers) of azobisisobutyronitrile (AIBN), is added eight volumes of a solution of the porogenic solvent, dodecyl alcohol and toluene (70:30). The solution so prepared is bubbled with nitrogen for 15 minutes and is used to fill a chromatography tube (50×8 mm I.D.) sealed with a rubber nut plug at the bottom end. The tube is then sealed at the top end with a rubber nut plug and the contents are allowed to polymerize at 70° C. for 24 hours.

Following polymerization, the rubber plugs are replaced by column end fittings and the column is connected to an HPLC system. The HPLC instrument has a low-pressure mixing quaternary gradient capability. A cartridge or guard column containing an iminodiacetate multivalent cation capture resin is placed in line between the column and the mobile phase source reservoir. The column is then washed by flowing 100 mL of tetrahydrofuran (THF) at 1 mL/min through the column to remove the dodecyl alcohol and toluene, thereby creating through-pores in the otherwise solid polymer monolith.

In this example, all of the flow paths are either titanium, sapphire, ceramic, or PEEK, except for the tube body, which is 316 stainless steel. The interior of the 316 stainless steel tube is passivated with dilute nitric acid prior to use.

EXAMPLE 11

Acid Wash Treatment To Remove Multivalent Metal Cation Contaminants

The non-polar, organic polymer monolith column is washed by flowing tetrahydrofuran through the column at a flow rate of 2 mL per minute for 10 minutes followed by flowing methanol through the column at 2 mL per minute for 10 minutes. The non-polar, organic polymer monolith column is washed further by flowing a mixture containing 100 mL of tetrahydrofuran and 100 mL of concentrated hydrochloric acid through the column at 10 mL per minute for 20 minutes. Following this acid treatment, the non-polar, organic polymer monolith column is washed by flowing tetrahydrofuran/water (1:1) through the column at 2 mL per minute until neutral (pH 7).

EXAMPLE 12

MIPC Analysis of an RNA Sizing Standard by MIPC using a 7.8 mm ID Column

Figure 26:
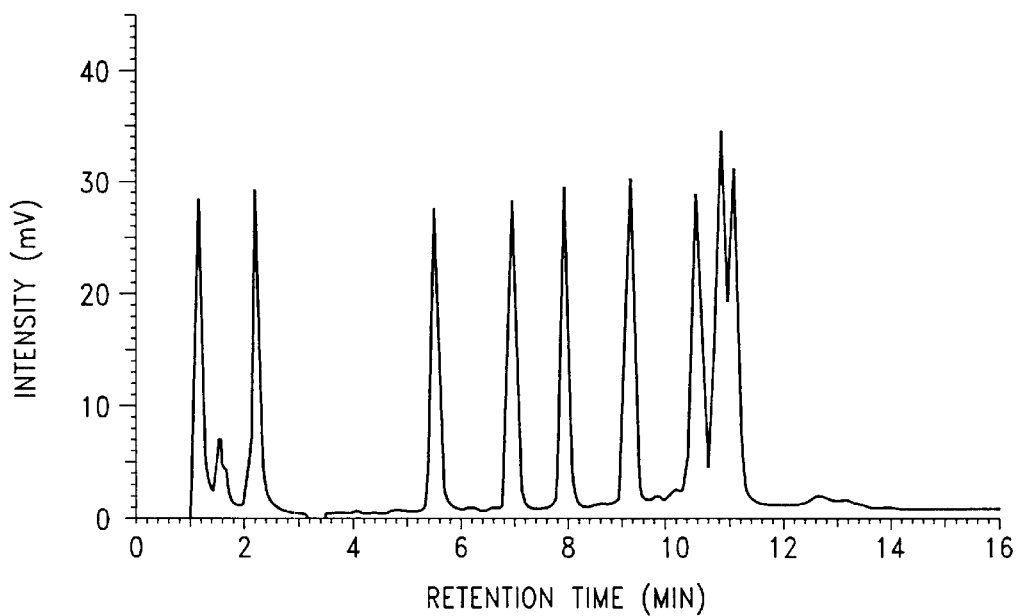
FIG. 26 illustrates an elution profile from MIPC analysis of RNA size markers carried out at a column temperature of 75° C.

MIPC analysis of an RNA ladder (Catalog no. 15623010, Life Technologies, containing single-stranded fragments of the following nuceotide lengths: 155, 280, 400, 530, 780, 1280, 1520, 1770) was performed using octadecyl modified, nonporous poly(styrene-divinylbenzene) beads packed in a 50 mm×7.8 mm ID reverse phase column (DNASEP® Cartridge, Transgenomic, Inc., San Jose, Calif.) and using a WAVE® Nucleic Acid Fragment Analysis System (Transgenomic) (FIG. 26). Buffer A: 0.1 M TEAA, pH 7.0; buffer B: 0.1 TEAA, 25% (v/v) acetonitrile, pH 7.0. The buffer stock solutions were obtained form Transgenomic. The gradient conditions were as follows:

| Time (min) | % B |
| --- | --- |
| 0.0 | 38 |
| 1.0 | 40 |
| 16 | 60 |
| 22 | 66 |
| 22.5 | 70 |
| 23 | 100 |
| 24 | 100 |
| 25 | 38 |
| 27 | 38 |

The flow rate was 0.9 mL/min and the column temperature was 40.0° C. UV detection was performed at 260 nm. The injection volume was 3.0 μL (3 μg RNA). The sample contained a mixture of eight RNAs having the nucleotide lengths as shown in FIG. 23.

Prior to the injection and elution of the RNA sample, the column was equilibrated with 75% acetonitrile for 30–45 min at a rate of 0.9 mL/min. The column was then equilibrated using 38% B for 30 min. Prior to the injection and elution of RNA, two control gradient elutions (using the same gradient conditions as for the RNA) were performed after a first injection of 10 μL of 0.5 mM EDTA and after a second injection consisting of 10 μL of nuclease free water (Catalog no. 9930, Ambion, Inc., Austin, Tex.). These two injections (data not shown) demonstrated that the column was free from contamination.

In preparing the RNA sample for injection, all chemicals were of the highest purity grade available for molecular biology. Solutions, glassware, and small instruments were sterilized whenever possible. Liquid transfers were made using RNase free pipette tips (Rainin Instrument Co., Inc., Woburn, Mass.). All manipulations were performed wearing surgical gloves.

EXAMPLE 13

Effect of Temperature on the Elution of RNA Sizing Standards

The MIPC analysis as described in Example 12 was repeated at column temperatures of 50.0° C. (FIG. 24), 65° C. (FIG. 25), and 75° C. (FIG. 26).

EXAMPLE 14

Effect of Cr(III) contamination on the segregation of an RNA ladder by MIPC at 75° C.

RNA ladder (Catalog no. 15623010, Life Technologies, Rockville, Md.) containing RNA at a concentration of 1 µg/pL was diluted with four portions of water to one portion of the 1 µg/µL solution prior to injection. The injection volume was 20 µL (containing 2 µg RNA).

Figure 27:
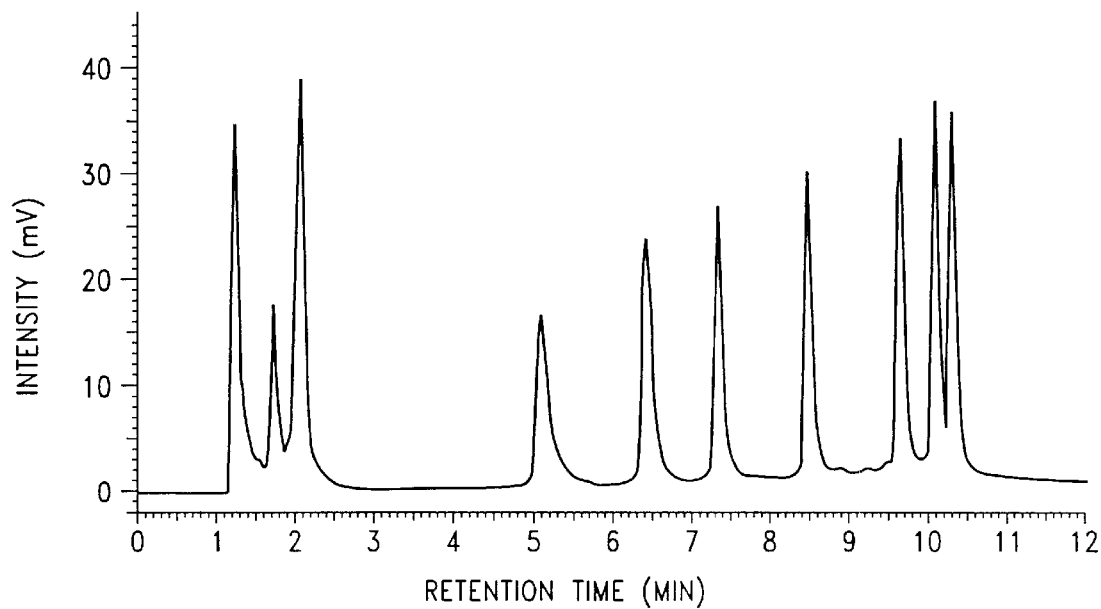
FIG. 27 illustrates an elution profile from a MIPC analysis of an RNA ladder carried out at a column temperature of 75° C.
Figure 28:
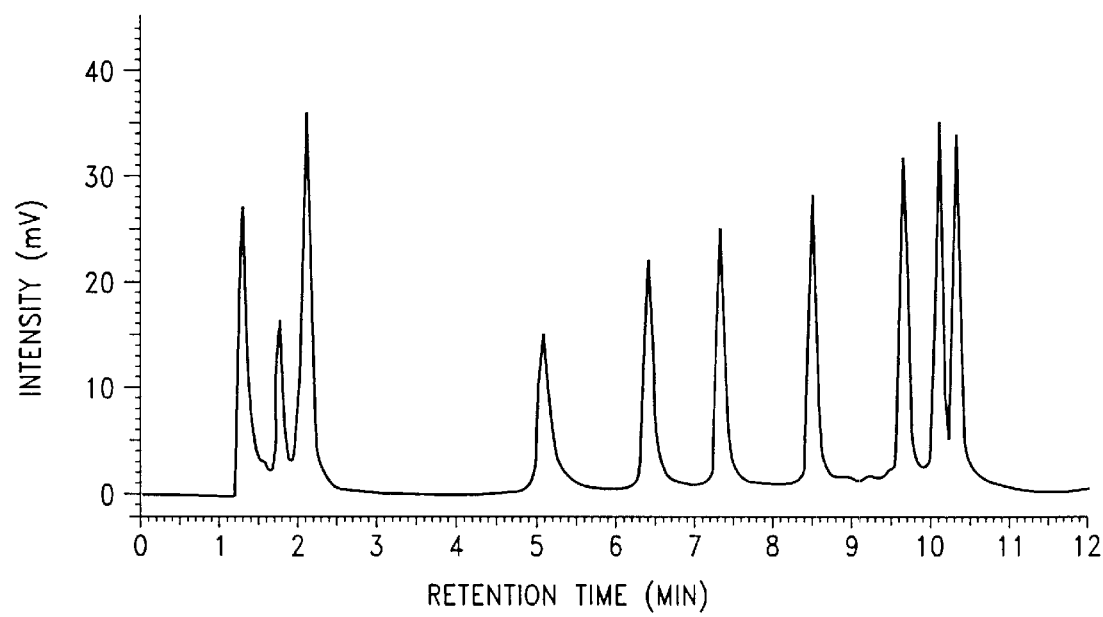
FIG. 28 illustrates an elution profile from a MIPC analysis of an RNA ladder carried out at a column temperature of 75° C. after a single injection of a Cr(III) solution onto the column used in FIG. 27.
Figure 29:
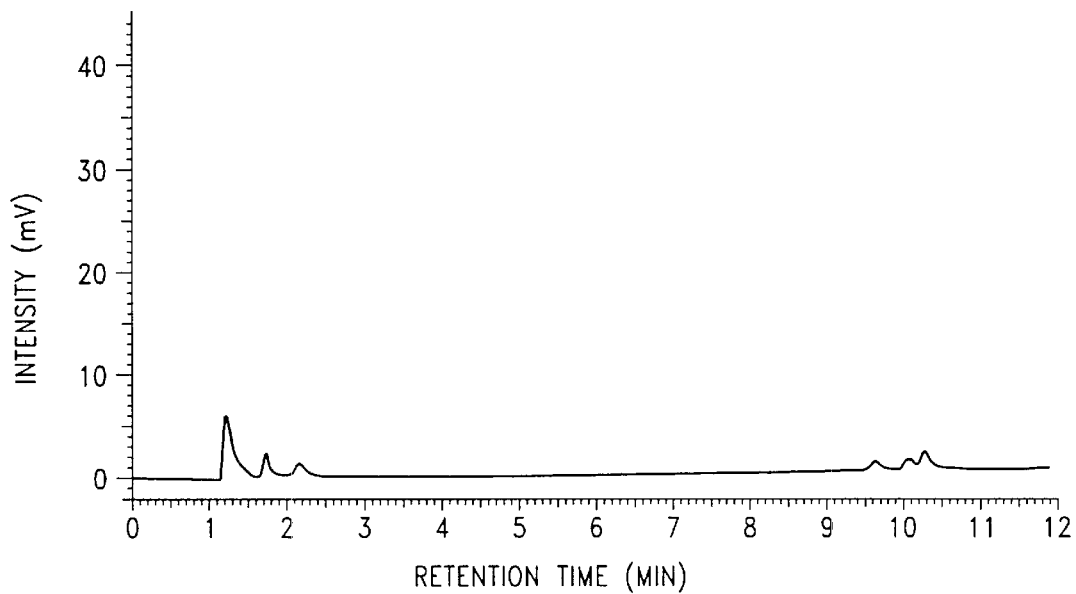
FIG. 29 illustrates an elution profile from a MIPC analysis of an RNA ladder carried out at a column temperature of 75° C. after five additional injections of a Cr(III) solution onto the column used in FIG. 28.
Figure 30:
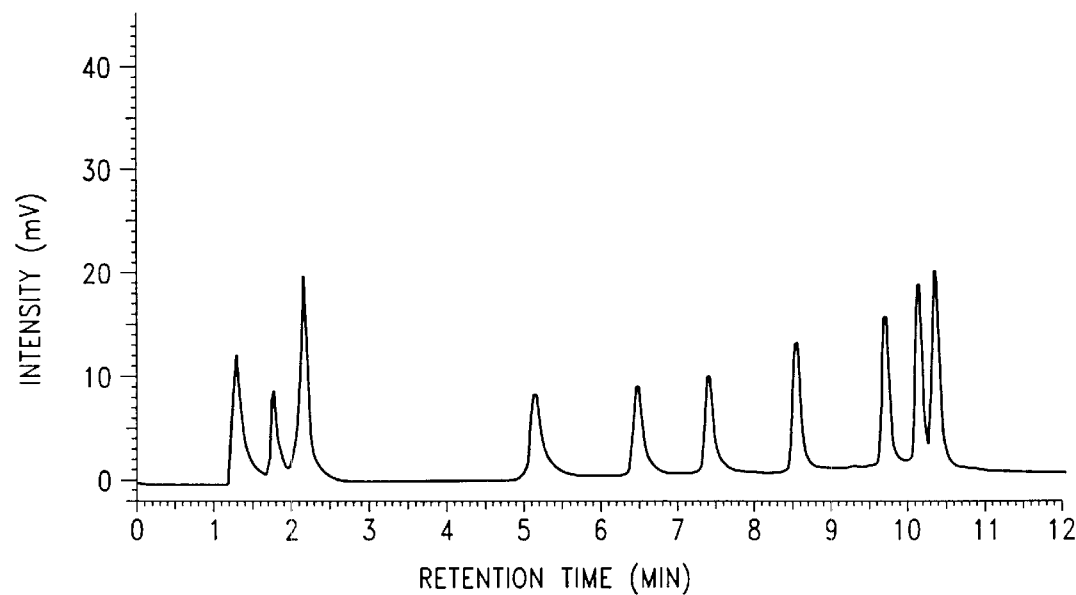
FIG. 30 illustrates an elution profile from a MIPC analysis of an RNA ladder carried out at a column temperature of 75° C. after one injection of an EDTA solution onto the column used in FIG. 29.
Figure 31:
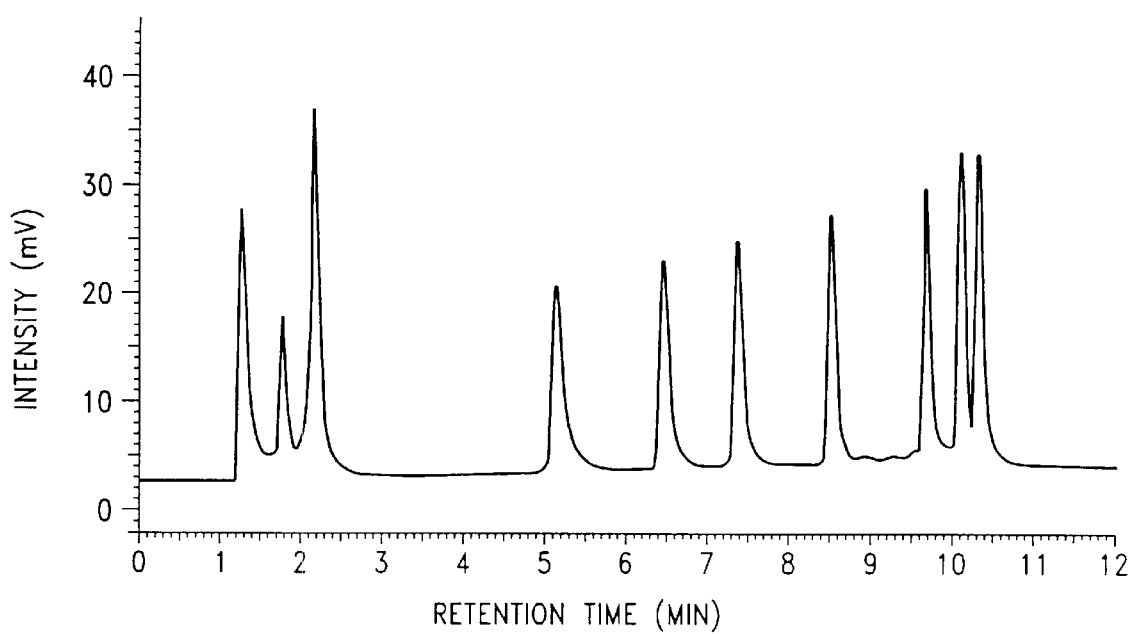
FIG. 31 illustrates an elution profile from a MIPC analysis of an RNA ladder carried out at a column temperature of 75° C. after five additional injections of an EDTA solution onto the column used in FIG. 30.

The segregation shown in FIG. 27 was obtained using a 50×7.8 mm ID column containing 2.2 µm alkylated poly(styrene-divinylbenzene) beads (DNASep®, Transgenomic). The chromatography system included a Waters Action Analyzer LC System, a Model 484 Tunable Absorbance Detector (Waters), a Model L7200 autosampler (Hitachi), a model L7300 oven (Hitachi), and the HSM Chromatography Data System (Hitachi). The mobile phase included buffer A: 0.1 M TEM, pH 7.3; buffer B: 0.1 M TEM and 25.0% acetonitrile; buffer C: 75% acetonitrile in water.

Prior to use, the entire chromatography system was cleaned, without a column connected, with 0.05 M EDTA solution overnight at 0.5 mL/min. After this cleaning, the solvent system channels A, B and C were cleaned and rinsed with DEPC treated water (Catalog no. 08-005Z, BioWhittaker, Walkersville, Md.). Prior to injection of RNA ladder, the column was connected and the system was cleaned using 100% of buffer C for 30 min at 0.9 mL/min at 75° C., followed by two injections of 0.5M EDTA (20 µL) (Catalog no. 750009, Research Genetics, Huntsville, Ala.) and two injections of water (20 µL). The column was eluted after each injection using the gradient as described below.

The gradient was as follows: a linear gradient of 38% to 40% B in 1 minute, followed by a linear gradient from 40% B to 56% B in 12 minutes, followed by a linear gradient of 56% to 100% B in 1 min, and then hold for 2 min. The flow rate was 0.75 mL/min.; UV detection was at 260 nm; and the column oven setting was 75° C.

The RNA fragments in the ladder were assigned the following elution times (FIG. 27): 2.05 min (0.155 kb), 5.04 min (2.8 kb), 6.35 min (4 kb), 7.26 min (5.3 kb), 8.41 min (7.8 kb), 9.58 min (1.28 kb), 10.02 min (1.52 kb), 10.23 min (1.77 kb).

The column was injected with 5 µL of 520 ppm Cr(III) solution and subjected to the same gradient. The Cr(III) solution was prepared by dissolving 0.125 g of $CrK(SO_4)_2 \cdot 12H_2O$ (Mallinckrodt Baker, Inc.) in 25 mL water. This was followed by another 20 µL injection of RNA ladder which gave the elution profile shown in FIG. 28. The total area under the eight RNA peaks in FIG. 28 was 94.6% as compared with the peaks in FIG. 27.

The column was then injected with five more 5 µL portions of the 520 ppm Cr(III) solution. Each of these was a continuous injection lasting about 0.8 min. The time between injections was 1.8 min. Before and after each injection, a constant mobile phase containing 10% B was passed through the column. After the last injection of Cr(III), a baseline in the UV absorbance was obtained, and another 20 µL of RNA ladder was injected giving the elution profile shown in FIG. 29, in which the peaks due to the RNA fragments were small or essentially undetectable.

The column was then injected with 10 µL of a 0.1 M solution of EDTA followed by gradient elution. The 0.1M EDTA solution was prepared by diluting the 0.5M solution of EDTA (Research Genetics) with water. This was followed by another 20 µL injection of RNA ladder which gave the elution profile shown in FIG. 30. The area under the peaks FIG. 30 was 47.9% as compared with the peaks in FIG. 27.

The column was then injected with five more 10 µL portions of the 0.1M EDTA solution. Each of these was a continuous injection (at a constant flow of 10% B) lasting about 0.8 min. After a constant baseline in the UV absorbance was obtained, another 20 µL of RNA ladder was injected which gave the elution profile shown in FIG. 31. The area under the peaks in FIG. 31 was 85.5% as compared with the peak in FIG. 27.

Buffers A, B, C, and the Cr(III) and EDTA solutions were prepared using DEPC treated water (BioWhittaker).

All references cited herein are hereby incorporated by reference in their entirety.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A reverse phase chromatographic method for segregating a mixture of RNA molecules having lengths exceeding about 100 nucleotides, said method comprising:
    a) applying a solution of said fragments and counterion reagent to a column containing polymeric beads having non-polar surfaces, wherein said beads have an average diameter of about 1 to about 100 microns wherein said surfaces are characterized by being substantially free from multivalent cations that are free to bind with said RNA;
    b) eluting said RNA molecules with a mobile phase which includes said counterion reagent and an organic component.

2. A method of claim 1 wherein said eluting is carried out at a minimum denaturing temperature.

3. A method of claim 1 including collecting mobile phase fractions containing said RNA molecules.

4. A method of claim 1 further including detecting RNA molecules during step (b).

5. A method of claim 1 wherein said segregating is performed by Matched Ion Polynucleotide Chromatography.

6. A method of claim 1 wherein said surfaces are characterized by being substantially free from multivalent cations which are free to interfere with RNA segregation.

7. A method of claim 1 wherein said multivalent metal cations are selected from the group consisting for Fe(III), Cu(II), Cr(III), and colloidal metal.

8. A method of claim 1 wherein said mobile phase includes a multivalent cation binding agent.

9. A method of claim 8 wherein said cation binding agent comprises EDTA.

10. A method of claim 1 wherein said medium comprises polymer beads having an average diameter of 0.5 to 100 microns, the non-polar surfaces being unsubstituted or having bound thereto a hydrocarbon group having from 1 to 1,000,000 carbons.

11. A method of claim 1, wherein said mobile phase comprises a counterion agent and an organic solvent, wherein said organic solvent is water soluble.

12. A method of claim 11, wherein said solvent is selected from the group consisting of alcohol, acetonitrile, dimethylformamide, tetrahydrofuran, ester, ether, and mixtures of one or more thereof.

13. A method of claim 11, wherein said solvent comprises acetonitrile.

14. A method of claim 1 wherein said counterion agent is selected from the group consisting of lower alkyl primary amine, lower alkyl secondary amine, lower alkyl tertiary amine, lower trialkyammonium salt, quaternary ammonium salt, and mixtures of one or more thereof.

15. A method of claim 14 wherein said counterion agent is selected from the group consisting of octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, triethylammonium hexafluoroisopropyl alcohol, and mixtures of one or more thereof.

16. A method of claim 1 wherein said medium has been subjected to acid wash treatment to remove any residual metal contaminants.

17. A method of claim 1 where said medium has been subjected to treatment with multivalent cation binding agent.

18. A method of claim 1 wherein said eluting is carried out at a temperature greater than about 60° C.

19. A method of claim 18 wherein said eluting is carried out at a temperature within the range of about 60° C. to about 90° C.

20. A method of claim 1 wherein the pH of said mobile phase is within the range of about pH 5 to about pH 9.

21. A method of claim 20 wherein the pH of said mobile phase is about pH 7.

22. A method of claim 1 wherein said mixture comprises RNA molecules exceeding about 1,000 nucleotides.

23. A method of claim 1 wherein said mixture comprises RNA molecules having up to about 20,000 nucleotides.

24. A chromatographic method for segregating a mixture of RNA molecules having lengths exceeding about 100 nucleotides, said method comprising:
  a) applying a solution of said fragments and counterion reagent to a column containing polymeric beads having non-polar surfaces, wherein said beads have an average diameter of about 1 to about 100 microns wherein said surfaces are characterized by being substantially free from multivalent cations that are free to bind with said RNA;
  b) eluting said RNA molecules at a minimum denaturing temperature.

25. A method of claim 24 wherein step (b) includes eluting said RNA molecules with a mobile phase which includes said counterion reagent and an organic solvent.

26. A method of claim 24 wherein said temperature is in the range of about 60° C. to about 100° C.

27. A method of claim 24 wherein said surfaces are characterized by being substantially free from multivalent cations which are free to interfere with RNA segregation.

28. A chromatographic method for segregating a mixture of RNA molecules having lengths exceeding about 100 nucleotides, said method comprising:
  a) flowing the mixture through a separation column containing polymer beads having an average diameter of 0.5 to 100 microns said beads having non-polar surfaces, said beads being unsubstituted polymer beads or polymer beads substituted with a moiety selected from the group consisting of hydrocarbon having from 1 to 1,000,000 carbons wherein said surfaces are characterized by being substantially free from multivalent cations that are free to bind with said RNA, and
  b) segregating said mixture of RNA molecules at a minimum denaturing temperature.

29. A chromatographic method for segregating a mixture of RNA molecules, said method comprising:
  a) flowing the mixture through a separation column containing polymer beads having an average diameter of 0.5 to 100 microns, said beads being unsubstituted polymer beads or polymer beads substituted with a moiety selected from the group consisting of hydrocarbon having from 1 to 1,000,000 carbons, wherein said beads are characterized by being substantially free from multivalent cations which are free to bind with said RNA molecules, and
  b) segregating said mixture of RNA molecules at a minimum denaturing temperature.

30. An improved method for segregating a mixture of RNA molecules by Matched Ion Polynucleotide Chromatography, said mixture comprising molecules having lengths exceeding about 100 nucleotides, the method comprising:
  a) applying a solution of said molecules and counterion reagent to a column containing polymeric separation beads having non-polar surfaces, wherein said separation beads have an average diameter of 1 to 100 microns, said column having an ID greater than about 5 mm wherein said surfaces are characterized by being substantially free from multivalent cations that are free to bind with said RNA;
  b) eluting said RNA molecules with a mobile phase which includes said counterion reagent and an organic component.

31. A method of claim 30 wherein said eluting is carried out at a temperature within the range of about 60° C. to about 90° C.

32. A method of claim 30 wherein said ID is greater than about 7 mm.

33. A method of claim 30 wherein said ID is greater than about 10 mm.

34. A method of claim 30 wherein said ID is greater than about 50 mm.

35. A method of claim 30 wherein said ID is in the range of about 5 mm to about 1 m.

36. A chromatographic method for segregating a mixture of RNA molecules having lengths exceeding about 100 nucleotides, said method comprising:
  a) applying a solution of said fragments and counterion reagent to a column containing polymeric beads having non-polar surfaces, wherein said beads have an average diameter of about 1 to about 100 microns, wherein said surfaces are characterized by being substantially free from multivalent cations which are free to bind with said RNA;
  b) eluting said RNA molecules with a mobile phase which includes said counterion reagent and an organic component.

37. A method of claim 36 wherein said eluting is carried out at a minimum denaturing temperature.

38. A method for segregating a mixture comprising RNA molecules, the method comprising:
  a) applying said mixture to a polymeric separation medium having non-polar surfaces, wherein said surfaces are characterized by being substantially free from multivalent cations which are free to interfere with RNA segregation, and
  b) eluting said RNA molecules with a mobile phase which includes counterion reagent and an organic component.

39. A method of claim 38 wherein said multivalent metal cations are selected from the group consisting of Fe(III), Cu(II), Cr(III), and colloidal metal.

40. A method of claim 38 wherein said medium has been subjected to acid wash treatment to remove any residual metal contaminants.

41. A method of claim 38 where said medium has been subjected to treatment with multivalent cation binding agent.

42. A method of claim 38 wherein step (b) includes, with a mobile phase containing a counterion agent, eluting said mixture at a minimum denaturing temperature.

43. A method of claim 42 wherein said eluting is carried out at a temperature greater than about 55° C.

44. A method of claim 43 wherein said eluting is carried out at a temperature within the range of about 60° C. to about 90° C.

45. A method of claim 38 wherein said medium comprises polymeric beads having non-polar surfaces, wherein said beads have an average diameter of about 1 to about 100 microns.

46. A method of claim 38 wherein the non-polar surfaces comprise the surfaces of interstitial spaces of a polymeric monolith.

47. A method of claim 46 wherein said surfaces are unsubstituted or substituted with a hydrocarbon group having from 1 to 1,000,000 carbons.

48. A method of claim 46 wherein said monolith comprises a member selected from the group consisting of monovinyl substituted aromatic compound, divinyl substituted aromatic compound, acrylate, methacrylate, polyolefin, polyester, polyurethane, polyamide, polycarbonate, fluoro-substituted ethylene, and combinations of one or more thereof.

* * * * *